United States Patent [19]

Venuti et al.

[11] Patent Number: 5,155,132
[45] Date of Patent: Oct. 13, 1992

[54] NAPHTHALENE LIPOXYGENASE-INHIBITING AGENTS

[75] Inventors: Michael C. Venuti, San Francisco; John M. Young, Redwood City, both of Calif.

[73] Assignee: Syntex (U.S.A.) Inc., Palo Alto, Calif.

[21] Appl. No.: 170,490

[22] Filed: Mar. 21, 1988

Related U.S. Application Data

[63] Continuation-in-part of Ser. No. 23,590, Mar. 9, 1987, Pat. No. 4,758,587.

[51] Int. Cl.$^5$ .............................................. A61K 31/27
[52] U.S. Cl. ..................................... 514/481; 514/510
[58] Field of Search ................. 514/481, 510; 558/266, 558/271; 560/31, 32, 115, 134; 568/633

[56] References Cited

U.S. PATENT DOCUMENTS

| | | | |
|---|---|---|---|
| 4,466,981 | 8/1984 | Jones | 424/311 |
| 4,758,587 | 7/1988 | Venuti | 514/481 |
| 4,758,587 | 7/1988 | Venuti | 514/481 |
| 4,786,652 | 11/1988 | Venuti | 514/481 |

FOREIGN PATENT DOCUMENTS

60-252441 12/1985 Japan .

*Primary Examiner*—Michael L. Shippen
*Attorney, Agent, or Firm*—Brian Lewis; David A. Lowin; Tom M. Moran

[57] ABSTRACT

Psoriasis in mammals is relieved by topically administering naphthalenes of the formula:

wherein:
$R^1$ is lower alkoxy or optionally substituted phenoxy;
$R^2$ is hydrogen, lower alkyl, optionally substituted phenyl or optionally substituted phenylalkyl;
$R^3$ is hydrogen, lower alkyl, lower alkoxy, halo, optionally substituted phenyl, optionally substituted phenyl-lower-alkyl or optionally substituted phenyl-lower-alkoxy, and m is 1 or 2;
X and Y are different and are either $R^4$ or —C(O)W wherein
$R^4$ is lower alkyl or optionally substituted phenyl-lower-alkyl;
W is —$OR^5$ or —$NR^6R^7$,
wherein
$R^5$ is alkyl, optionally substituted phenyl or optionally substituted benzyl; and $R^6$ and $R^7$ are independently hydrogen, lower alkyl, cycloalkyl or optionally substituted phenyl.

The compounds of this invention are also useful for the treatment of disease-states caused by lipoxygenase activity in mammals, particularly 5-lipoxygenase activity, when administered systemically.

2 Claims, No Drawings

NAPHTHALENE LIPOXYGENASE-INHIBITING AGENTS

This is a continuation-in-part of U.S. patent application Ser. No. 023,590, filed Mar. 9, 1987 now U.S. Pat. No. 4,758,587, the complete disclosure of which is hereby incorporated by reference.

BACKGROUND OF THE INVENTION

1. Field of the Invention

The invention relates to naphthalene derivatives which are useful in the treatment of certain dermatological conditions and in inhibiting lipoxygenase activity, particularly 5-lipoxygenase activity. Thus the compounds are useful both for topical treatment of inflammatory states in mammals and for systemic treatment of a variety of disease-states, including inflammation and hypersensitivity, caused by lipoxygenase activity in mammals, particularly 5-lipoxygenase activity. This invention also relates to pharmaceutical compositions useful in topically relieving the effects of certain chronic recurrent papulosquamous dermatoses, e.g., psoriasis, and in systemically relieving a variety of disease-states (including inflammatory states caused by an influx of leukocytes) caused by lipoxygenase activity, particularly 5-lipoxygenase activity. This invention also relates to a process for preparing compounds of this invention.

2. Related Disclosures

Psoriasis is a skin disease characterized in part by excessive proliferation of cells of the epidermis which remain strongly adherent and build up into a scaley plaque typical of the disease. While currently available therapies, such as corticosteroids, vitamin A derivatives (retinoids), cancer chemotherapeutic agents (methotrexate, razoxane), coal tar and anthralin preparations, and psoralen-u.v. irradiation (PUVA) are effective in controlling the disease to a certain extent, they can cause numerous and sometimes severe undesirable side effects including renal irritation, hepatic toxicity, and erythema.

Certain naphthoquinone derivatives are known to be useful in treating psoriasis. See, for example, U.S. Pat. Nos. 4,229,478, 4,466,981 and 4,593,120 and British Patent No. 1,243,401. Carbamate and carbonate derivatives of naphthalene having insecticidal properties are known. See, for example, U.S. Pat. Nos. 2,383,392, 3,958,006 and 4,181,741. Surprisingly, it has been discovered that the compounds of the instant invention are also effective antipsoriatic agents. Compounds of formula (I) provide prolonged activity in the treatment of psoriasis because of their stability upon application and slow conversion to compounds of formula (XII) and (XIII). Further, the compounds of the present invention are more stable in the topical formulations normally used.

In addition, it has been surprisingly discovered that the compounds of formula (I) are systemically effective in the inhibition of lipoxygenase activity in mammals, particularly 5-lipoxygenase activity. They are thus useful in relieving a variety of disease-states, including inflammatory states and hypersensitivity, caused by such lipoxygenase activity.

SUMMARY

The present invention relates to a compound of the formula

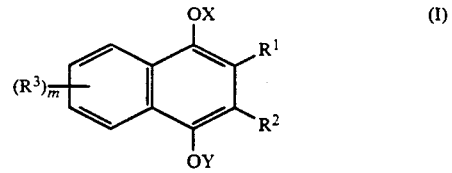

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are either $R^4$ or $-C(O)W$ wherein $R^4$ is lower alkyl of one to six carbon atoms or phenyl-lower-alkyl of one to six carbon atoms, wherein the phenyl ring is optionally substituted by one or two substituents chosen from lower alkyl of one to four carbon atoms, lower alkoxy of one to four carbon atoms and halo; and W is $-OR^5$ or $-NR^6R^7$, wherein $R^5$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^6$ and $R^7$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

Another aspect of the invention is a method for relieving inflammatory diseases such as the condition of psoriasis in a mammal which comprises topically administering to said mammal an antiinflammatory amount of a compound of formula (I).

Yet another aspect of the invention is a method for relieving a variety of disease-states, including the conditions of inflammatory and hypersensitivity, caused by lipoxygenase activity in a mammal, particularly 5-lipoxygenase activity, which method comprises systemically administering to the said mammal a lipoxygenase inhibiting amount of a compound of formula (I).

A further aspect of the present invention relates to a pharmaceutical composition in a form suitable for topical administration to mammals comprising a compound of the formula (I) in admixture with one or more pharmaceutically acceptable non-toxic carriers.

Still another aspect of the present invention relates to a pharmaceutical composition in a form suitable for systemic administration to mammals comprising a compound of the formula (I) in admixture with one or more pharmaceutically acceptable non-toxic carriers.

Another aspect of the invention is a novel process for preparing compounds of formula (I). Compounds of formula (VIII) and (IX) infra, which are intermediates for compounds of formula (Ia), (Ib), (Ic) and (Id) infra, are prepared by carefully controlled hydrolysis of the compound of formula (VII). Compounds of formula (Ia), (Ib), (Ic) and (Id) are prepared by reacting compounds of formula (VIII) and (IX) with the appropriate reactant.

DETAILED DESCRIPTION AND PREFERRED EMBODIMENT

In its broadest aspect, the present invention relates to a compound of the formula

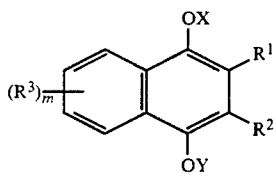

wherein:
$R^1$ is lower alkoxy of one to six carbon atoms or phenoxy optionally substituted by one or two substituents chosen from lower alkyl of one to four carbon atoms, lower alkoxy of one to four carbon atoms and halo;
$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;
$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;
m is 1 or 2; and
X and Y are different and are either $R^4$ or —C(O)W wherein
$R^4$ is lower alkyl of one to six carbon atoms or phenyl-lower-alkyl of one to six carbon atoms, wherein the phenyl ring is optionally substituted by one or two substituents chosen from lower alkyl of one to four carbon atoms, lower alkoxy of one to four carbon atoms and halo; and
W is —$OR^5$ or —$NR^6R^7$, wherein
$R^5$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and
$R^6$ and $R^7$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

The present invention also relates to a method for relieving inflammatory diseases such as the condition of psoriasis in a mammal which comprises topically administering to said mammal an antiinflammatory amount of a compound of formula (I).

Yet another aspect of the invention is a method for relieving a variety of disease-states, including the conditions of inflammation and hypersensitivity, caused by lipoxygenase activity in a mammal, particularly 5-lipoxygenase activity, which comprises systemically administering to said mammal a lipoxygenase inhibiting amount of a compound of formula (I).

A further aspect of the present invention relates to a pharmaceutical composition in a form suitable for topical administration to mammals comprising a compound of the formula (I) in admixture with one or more pharmaceutically acceptable non-toxic carriers.

Still another aspect of the present invention relates to a pharmaceutical composition in a form suitable for systemic administration to mammals comprising a compound of the formula (I) in admixture with one or more pharmaceutically acceptable non-toxic carriers.

The compounds of formula (I) may be divided into subgroups (Ia), (Ib), (Ic) and (Id).

Compounds of subgroup (Ia) and (Ib) are represented by formula (I) wherein one of X and Y is $R^4$ and the other is —C(O)$NR^6R^7$ wherein $R^1$, $R^2$, $R^3$, $R^4$, $R^6$, $R^7$ and m are as defined above. Within this subgroup it is preferred that $R^4$ is lower alkyl of one to three carbon atoms such as methyl, ethyl, n-propyl and i-propyl, with methyl being most preferred.

Compounds of subgroup (Ic) and (Id) are represented by formula (I) wherein one of X and Y is $R^4$ and the other is —C(O)$OR^5$ wherein $R^1$, $R^2$, $R^3$, $R^4$, $R^5$ and m are as defined above. Within this subgroup it is preferred that $R^4$ is lower alkyl of one to three carbon atoms such as methyl, ethyl, n-propyl and i-propyl, with methyl being most preferred.

An even more specific embodiment of the instant invention are compounds of formula (I) wherein m is 1 and $R^3$ is at the 6-position and is bromo, chloro, fluoro, methoxy, ethoxy. n-propoxy, i-propoxy, n-butoxy, and i-butoxy, with chloro being most preferred.

A preferred embodiment of the invention are compounds of formula (I) wherein $R^3$ is hydrogen.

Another embodiment of the invention are compounds wherein m is 2 and the two $R^3$s are at the 6 and 7 positions and are lower alkyl, lower alkoxy or halo with $R^3$ being methyl being preferred.

In the present specification and claims the term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, n-heptyl, 2,2-dimethylbutyl and 3,3-dimethylpentyl. The term "lower alkyl" refers to alkyl groups of one to six carbon atoms as defined above. Examples of "lower alkyl" groups are methyl, ethyl, n-propyl, i-propyl, n-butyl, i-butyl, s-butyl, 2,2-dimethylpropyl and t-hexyl. The term "phenyl-lower-alkyl" refers to an optionally substituted phenyl ring attached to an alkylene chain of one to six carbon atoms.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy. "Phenyl-lower-alkoxy" refers to a phenyl ring attached to an alkylene chain of one to six carbon atoms having bonded thereto an oxygen atom. Examples of "phenyl-lower-alkoxy" are benzyloxy, 4-chlorophenylethoxy and phenyl-n-propoxy and 2-methoxyphenyl-n-hexyloxy.

The term "sterically hindered" refers to alkyl groups wherein branching occurs at the carbon adjacent to or one carbon removed from the carbonyl group or to optionally substituted phenyl.

Optionally substituted phenyl refers to a phenyl ring optionally substituted by one or more substituents selected from the group consisting of lower alkyl, lower alkoxy and halo unless otherwise defined.

The term "halo" refers to fluoro, chloro, and bromo.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The compounds of formula (I) are defined to show, in part, $R^1$ as lower alkoxy and $R^4$ as lower alkyl. In this situation, as $R^4$ is always attached to oxygen, it can be readily understood that $R^1$ and $-OR^4$ both represent lower alkoxy.

The compounds of formula (I) exist as two pairs of regioisomers (position isomers) represented by the formulas (Ia) and (Ib), and (Ic) and (Id). The isomers may be separated at any stage of the preparation of (Ia), (Ib), (Ic) and (Id), but it is preferred to separate the isomeric mixture of compounds of formula (Ia) and (Ib). The individual isomers of compounds of formula (Ic) and (Id) may then be prepared. The isomers may be separated by crystallization, normal or reverse phase HPLC or other partition chromatographic techniques, and the like.

The claims and specification of this patent application are intended to encompass each individual isomer of formula (Ia), (Ib), (Ic) and (Id) alone or in combination with its regioisomer, unless specifically designated otherwise.

It is possible that the preparation of compounds of formula (II) where both $R^2$ and $R^3$ are other than hydrogen may give rise to a mixture of two isomers, i.e. the two isomers where $R^2$ is at the 2- or the 3-position of the compound of formula (II). Without separation, this would lead eventually to a mixture of 2- and 3-isomers of the compound of formula (I). In the event that such a mixture is obtained, the isomers may be separated by crystallization, normal or reverse phase HPLC or other partition chromatographic techniques, and the like. The claims and specification of this patent application are intended to encompass each individual isomer of formula (I) alone or in combination with its corresponding isomer, unless specifically designated otherwise.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthalenes of formula (I) may be formulated with suitable pharmaceutical vehicles known in the art to form particularly effective topical compositions. An effective amount of the naphthalene compound is about 0.001% w to about 10% w of the total formulated composition. The rest of the formulated composition will be about 90% w to about 99.999% w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50-99 parts by weight |
| Fatty Alcohol | 1-20 |
| Non-ionic Surfactant | 0-10 |
| Mineral Oil | 0-10 |
| Typical Pharmaceutical Adjuvants | 0-5 |
| Active Ingredients | 0.001-10 |

The fatty alcohol, non-ionic surfactant, and other adjuvants are discussed in U.S. Pat. No. 3,934,013 to Poulsen.

The naphthalenes of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | | |
|---|---|---|
| White Petrolatum | 40-94 | parts by weight |
| Mineral Oil | 5-20 | |
| Glycol Solvent | 1-15 | |
| Surfactant | 0-10 | |
| Stabilizer | 0-10 | |
| Active Ingredients | 0.001-10.0 | |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". Following is a typical ointment base formulation containing propylene carbonate:

| Active Ingredients | 0.001–10.0 parts by weight |
|---|---|
| Propylene Carbonate | 1–10 |
| Solvent | 1–10 |
| Surfactant | 0–10 |
| White Petrolatum | 70–97 |

Suitable solvents, surfactants, stabilizers, etc. are discussed in U.S. Pat. No. 3,934,013.

A suitable topical "non-classical" anhydrous, water washable "ointment type" base is described in U.S. Pat. No. 3,592,930 to Katz and Neiman. A representative composition of this invention utilizing such base is as follows:

| Glycol Solvent | 40–35 parts by weight |
|---|---|
| Fatty Alcohol | 15–45 |
| Compatible Plasticizer | 0–15 |
| Compatible Coupling Agent | 0–15 |
| Penetrant | 0–20 |
| Active Ingredients | 0.001–10.0 |

Another aspect of the invention is a method for relieving the condition of psoriasis in a mammal by topically administering a composition containing a compound of formula (I) wherein $R^1$, $R^2$, $R^3$, X, Y and m are as defined above. Generally, the anti-psoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed hereinabove, which is then placed in contact with the afflicted area(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

The compounds of the present invention have also been found to be active when administered systemically for the treatment of mammals having a variety of disease-states caused by lipoxygenase activity, particularly 5-lipoxygenase activity. Accordingly, the compounds may be formulated as oral, parenteral and otherwise systemic compositions. Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages.

The compositions will include a conventional pharmaceutical carrier or excipient and a therapeutically effective amount of a compound of formula (I) and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician.

Typical compositions contain 0.01–95% by weight of active ingredient, with the balance one or more acceptable non-toxic carriers. The percentage of active ingredient, will, of course, depend upon the dosage form and the mode of administration.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffereing agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 2%–95% active ingredient, preferably 5–25%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For systemic administration via suppository, traditional binders and carriers include, e.g. polyalkalene glycols or triglycerides. Such suppositories may be formed from mixtures containing active ingredient in the range of 0.1%–10%; preferably 0.5 to 2%.

In vitro lipoxygenase inhibiting activity of the compounds of this invention are determined by the standard Human Polymorphonuclear Leukocytes assay. This assay is a modification of that described by O. Radmark, C. Malmsten, and B. Samuelsson in *FEBS Letter*, 110, 213–215, 1980. In vivo lipoxygenase inhibiting activity of the compounds of this invention are determined by the arachidonic acid mouse ear inflammation assay as described by J. M. Young, D. A. Spires, C. J. Bedord, B. Wagner, S. J. Ballaron and L. M. DeYoung in *Journal of Investigative Dermatology*, 82, 367–371, 1984.

PREPARATION

The compounds of formula (Ia), (Ib), (Ic) and (Id) may be prepared from the compounds of formula (XII) and (XIII), which are prepared as shown below in Reaction Sequence I.

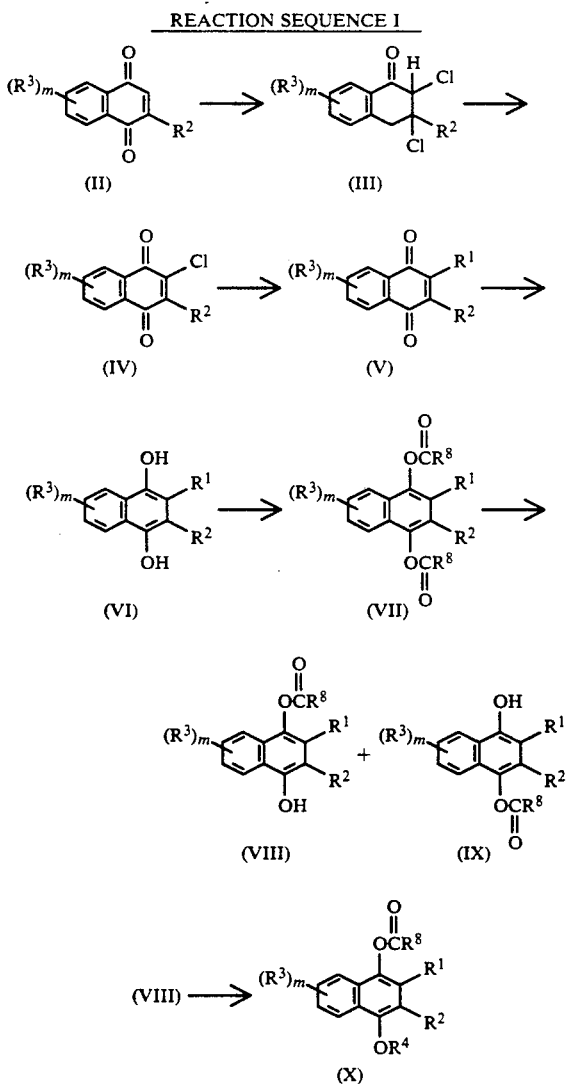

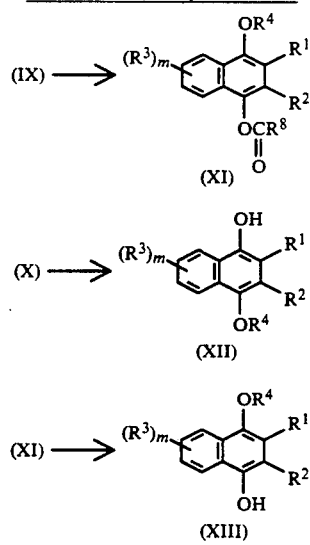

wherein $R^1$, $R^2$, $R^3$, $R^4$ and m are as defined above and $R^8$ is alkyl, phenyl or benzyl.

The intermediates of formula (II), where $R^2$ is hydrogen and $R^3$ is as defined above are prepared according to the method disclosed in J. Am. Chem. Soc., 70, 3165 (1948) and Ibid., 71, 3615 (1949). A butadiene optionally substituted with the appropriate embodiment of $R^3$ is reacted with 1,4-benzoquinone in a solvent such as acetic acid at a temperature of −10° C. to 30° C., preferably at 25° C. for 24 to 72 hours, preferably from 40 to 48 hours. The 5,8-dihydro derivative of the compound of formula (II) is recovered and treated with an oxidizing agent such as sodium dichromate, sodium nitrite, manganese dioxide and the like to form compounds of formula (II) wherein $R^2$ is hydrogen. Compounds of formula (II) wherein $R^2$ is alkyl, optionally substituted phenyl or phenylalkyl may be prepared by reacting the naphthoquinone of formula (II) wherein $R^2$ is hydrogen with an acid of the formula $R^2COOH$ wherein $R^2$ is as defined above but is other than hydrogen. A solution of the acid and naphthoquinone in acetonitrile and sulfolane in the presence of a metal nitrate, e.g. silver nitrate and the like, is heated to 50°–100° C., preferably to 55°–75° C. A solution of a persulfate salt, e.g. diammonium persulfate, is added dropwise. Compounds of formula (II) wherein $R^2$ is alkyl, optionally substituted phenyl or phenylalkyl are recovered by conventional means such as chromatography.

Compounds of formula (III) are prepared by bubbling chlorine gas into a solution of compound of formula (II) dissolved in a solvent such as glacial acetic acid, nitrobenzene, carbon tetrachloride and the like, preferably glacial acetic acid at room temperature. The compound of formula (III), which may be isolated by known means, dissolved in a solvent such as acetic acid is treated with a suitable catalyst such as sodium acetate, iodine, iron (III) chloride, dimethylformamide or lower alcohols, for example methanol or ethanol, with heating under reflux for ½ to 4 hours, preferably for 1 to 2½ hours to yield compounds of formula (IV).

Compounds of formula (V) are prepared by reacting compound of formula (IV) with an alkali metal alkoxide or phenoxide such as sodium alkoxide or phenoxide, e.g., sodium methoxide or phenoxide in an anhydrous solvent such as methanol, dimethylformamide and the like, the solvent if an alcohol being chosen according to the length of the alkyl chain on the alkoxy group e.g. sodium methoxide in methanol, sodium ethoxide in ethanol and the like. The reaction mixture is heated at a temperature of about 0° C. to 60° C., preferably about 20° C. to 30° C., for 3 to 24 hours, preferably about 10 to 18 hours. Compounds of formula (V) are recovered by conventional means such as by crystallization.

Compounds of formula (IV) may also be converted to compounds of formula (V), by treatment with an alcoholic solution of a strong base such as potassium hydroxide in methanol and then alkylating the intermediate compound of formula (IX), infra, using the appropriate halide or an alcohol as is described hereinafter under Reaction Sequence II.

Compounds of formula (VII) are prepared from compounds of formula (V) by first hydrogenating to form compounds of formula (VI). The compound of formula (V) is hydrogenated in a hydrogen atmosphere in the presence of a catalyst such as palladium on charcoal, or alternatively using transfer hydrogenation conditions with, for example, cyclohexadiene and a catalyst such as palladium on charcoal. Polar solvents such as tetrahydrofuran, dimethylformamide or ethanol are preferred, most preferably tetrahydrofuran. Alternatively, the compounds of formula (V) are reduced with sodium hydrosulfite in an alcoholic solvent, preferably methanol or ethanol, to give the compound of formula (VI).

The compound of formula (VI) is then reacted with an acylating agent such as an appropriate anhydride, for example acetic anhydride, propanoic anhydride, benzoic acid anhydride and the like, preferably acetic anhydride, in the presence of an organic base such as pyridine, triethylamine and the like or an inorganic base such as sodium hydroxide, potassium carbonate, sodium bicarbonate and the like, preferably triethylamine, in an inert solvent such as benzene, acetonitrile, ethyl acetate, tetrahydrofuran, diethyl ether, chloroform, methylene chloride and the like. Acyl halides may also be used to acylate compounds of formula (VI) but acyl anhydrides are preferred. Compounds of formula (VII) are isolated by conventional means, preferably crystallization.

The compounds of formula (VIII) and (IX), i.e., compounds wherein either X or Y is hydrogen and the other X or Y is acyloxy, preferably acetyloxy, are prepared from the compounds of formula (VII) by a novel hydrolysis process wherein the pH of the reaction mixture is carefully controlled and maintained at pH 7.5 to 9.5, preferably pH 8-9. If general hydrolysis conditions are employed both ester groups are removed from the compound of formula (VII) to form the compound of formula (VI) which will revert to the 1,4-naphthoquinone under aerobic conditions.

The compound of formula (VII), dissolved in a mixture consisting of a pH 8-9 buffer solution such as a phosphate buffer solution and the like, and a solvent such as acetonitrile, dimethylformamide and the like, is heated to 40° C. to 120° C., preferably to 50° C. to 100° C. for 1 to 15 days, preferably for 2 to 12 days. The reaction is monitored by, e.g., thin layer chromatography. Additional buffer is added, if necessary, to maintain pH 8-9. The compounds of formula (VIII) and (IX) are recovered by, e.g., extraction and purified by recrystallization. The mixture of compounds of formula (VIII) and (IX) is separated by preparative high pressure liquid chromatography using silica gel and eluting with suitable solvents, for example anhydrous methanol/hexane.

Compounds of formula (X) or (XI) may be prepared by reacting a compound of formula (VIII) or (IX) respectively with an alkylating agent such as an alkyl tosylate, an alkyl mesylate or an alkyl or phenylalkyl halide such as benzyl bromide, i-propyl bromide, n-butyl bromide, phenylethyl bromide and the like.

To a solution of a compound of formula (VIII) or (IX) and an alkylating agent such as an alkyl or arylalkyl halide in a solvent such as tetrahydrofuran, dimethylformamide and the like, is added an equivalent amount of an amine base such as 1,8-diazobicyclo[5.4.-0]undec-7-one (DBU). The solution is maintained between 0° C. and 120° C., preferably between room temperature and 60° C. for ½ hour to five hours, preferably for 1 hour to 3 hours. The compound of formula (X) or (XI) is recovered by, e.g., evaporation followed by chromatography.

Compounds of formula (X) or (XI) may also be prepared by reacting the compound of formula (VIII) or (IX) with a diazoalkane such as diazomethane, diazoethane, diazophenylmethane and the like.

Compounds of formula (X) or (XI) wherein either X or Y is methyl are preferably prepared by reacting compound of formula (VIII) or (IX) with diazomethane.

A solution of the compound of formula (VIII) or (IX) in a solvent such as ether is treated with a solution of diazomethane in a solvent such as ether generated in situ from N-methyl-N-nitroso-p-toluenesulfonamide (Diazald ®). The compound of formula (X) or (XI) is recovered by evaporation followed by flash chromatography over silica gel.

Compounds of formula (XII) or (XIII) are prepared from the compounds of formula (X) and (XI) by hydrolysis of the ester group —OC(O)CH$_3$. Typically, the compound of formula (X) or (XI) is dissolved in a water-miscible solvent such as ethanol containing a base such as sodium hydroxide or potassium carbonate, optionally in the presence of water, and stirred at a temperature of about 0° C. to 80° C., preferably about 25° C., for about 1 to 24 hours, preferably about 6 hours. When the reaction is substantially complete, the compound of formula (XII) or (XIII) is separated by conventional means, such as recrystallization.

DBU and Diazald ® are available from, i.a., Aldrich Chemical Co. The alkyl and arylalkyl halides are readily available from, i.a., Aldrich Chemical Co. or may be made by methods well known in the art.

The butadiene intermediate, such as 2-chloro-1,3-butadiene (chloroprene), 2-methyl-1,3-butadiene(isoprene), 2-ethyl-1,3-butadiene 1-methoxy-1,3-butadiene, 2-phenyl-1,3-butadiene, 1-phenyl-1,3-butadiene and the like are available from, i.a., Pfaltz and Bauer Chemical Co. 2-Bromo-1,3-butadiene and 2-fluoro-1,3-butadiene may be prepared by methods well known in the art, for example, by the methods discussed in J. Am. Chem. Soc., 55 786 (1933) and U.S. Pat. No. 2,401,850, respectively.

The acid anhydrides are commercially available from, i.a., Aldrich Chemical Co. or if not available may be prepared by condensing the appropriate acid in the presence of acetic anhydride or acetyl chloride containing a trace of phosphoric acid. The anhydride is recovered by distillation or crystallization.

An alternative method for preparing the compounds of formula (V) is depicted in Reaction Sequence II below.

REACTION SEQUENCE II

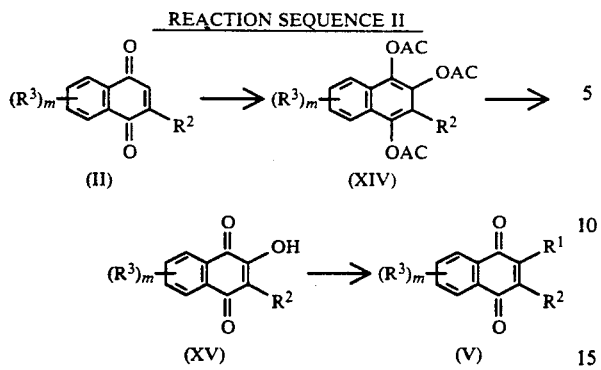

wherein $R^1$, $R^2$, $R^3$ and m are as defined above.

The compound of formula (XIV) is prepared by acylating the compound of formula (II) in the presence of a Lewis acid such as boron trifluoride:etherate or a strong inorganic acid, such as perchloric acid, and the like. This reaction is commonly known as the Theile-Winter reaction. The acylating agent is an acid anhydride such as acetic anhydride, propanoic anhydride and the like, preferably acetic anhydride. The compound of formula (XIV) wherein $R^2$ is hydrogen may be converted to the compound of formula (XIV) wherein $R^2$ is alkyl, optionally substituted phenyl or phenylalkyl by reaction with a peracid anhydride of the formula $(R_2CO_2)_2$ wherein $R^2$ is as defined above and is other than hydrogen. A solution of the unsubstituted compound in a solvent such as glacial acetic acid is heated to 70°–120° C., preferably from 75°–100° C. and an ethereal solution of the anhydride is added dropwise over 1 to 6 hours, preferably over 2 to 4 hours. The compound of formula (XIV) wherein $R^2$ is alkyl, optionally substituted phenyl or phenylalkyl is recovered by precipitation. The compound of formula (XIV) wherein $R^2$ is hydrogen or alkyl, optionally substituted phenyl or phenylalkyl is then hydrolyzed by treatment with an alkali metal alkoxide in an alcohol, such as sodium methoxide in methanol, followed by treatment with aqueous hydrochloric acid to form the compound of formula (XV).

The compound of formula (XV) is then converted to the compound of formula (V) by reaction with an appropriate halide and base, or an appropriate alcohol, for example methanol, ethanol and the like, under acid catalysis.

The compound of formula (XV) is reacted with an alkyl halide, e.g. an alkyl bromide or alkyl iodide in a solvent such as tetrahydrofuran and the like. A solution of 1,5-diazobicyclo[5.4.0]undec-5-ene (DBU) in a solvent such as tetrahydrofuran is added dropwise. The precipitate of DBU-hydrogen halide which forms is removed by filtration and the compound of formula (V) is recovered by evaporation.

The compound of formula (V) may also be prepared by reacting the compound of formula (XV) with an alcohol. To a solution of the compound of formula (XV) in the appropriate alcohol of formula $R^1OH$ is added boron trifluoride etherate. The solution is heated from 50° to 100° C., preferably from 60° to 80° C. for ½ hour to 4 hours, preferably for 1 to 3 hours. The compound of formula (V) is recovered by filtration.

An alternative method of preparing compounds of formula (XII) where $R^1$ is the same as $OR^4$ is from the compound of formula (VI) or (VII) as shown in Reaction Sequence III.

REACTION SEQUENCE III

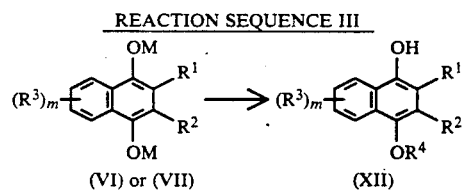

where M is hydrogen or acetyl and $R^1$, $R^2$, $R^3$, $R^4$ and m are as defined above.

The compound of formula (VI) or (VII) is dissolved in an alcohol of formula $R^1H$ containing anhydrous hydrochloric acid and the mixture stirred at about 60° C. for about 3 minutes. Ice water is added and the precipitate filtered off and dried under reduced pressure to give the compound of formula (XII) where $R^1$ is the same as $OR^4$. The reaction is discussed in more detail in J. Org. Chem. 34, 2788 (1969).

Compounds of Formula I

The preparation of the compounds of formula (Ia) and (Ib), where one of X and Y is $R^4$ and the other X or Y is $-C(O)NR^6R^7$, is shown in Reaction Sequences IVA, IVB and IVC below and the subsequent description. The Reaction Sequences are illustrated by reference to the preparation of the compound of formula (Ia), but are of course equally applicable to the preparation of the compound of formula (Ib).

REACTION SEQUENCE IVA

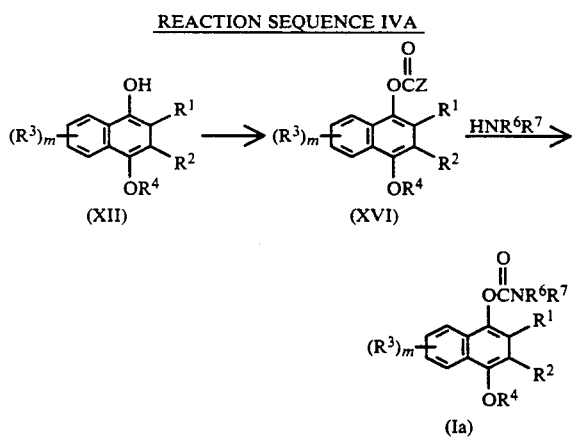

REACTION SEQUENCE IVB

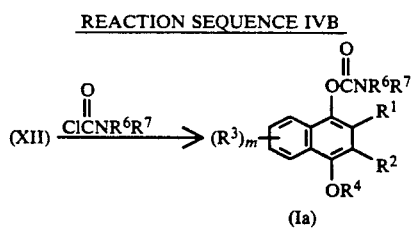

REACTION SEQUENCE IVC

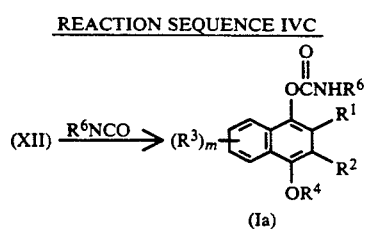

In Reaction Sequence IVA the preparation starts from the compound of formula (XII), prepared as shown in Reaction Sequences I, II and III. To prepare the compound of formula (Ia), where W is —$NR^6R^7$, the compound of formula (XII) is first converted to an activated carbonyl derivative of formula (XVI), in which Z is a leaving group chosen to be capable of displacement by an amine of formula $HNR^6R^7$. For example, Z may be halo, 1-imidazolyl, trichloromethoxy, optionally substituted phenoxy, such as 2,4-dichlorophenoxy, 4-methoxyphenoxy, and the like. For example, the compound of formula (XVI) where Z is chloro is made by reaction of a compound of formula (XII) with from 1–10 molar equivalents, preferably about 2 molar equivalents, of phosgene in an inert organic solvent as defined above, preferably benzene. The reaction takes place in the presence of from 1–5 molar equivalents, preferably about 2 molar equivalents of a tertiary organic base such as triethylamine or preferably pyridine. The reaction is conducted at from 0°–50° C., preferably about 25° C., for about 1–72 hours, preferably about 18 hours, and then filtered. Evaporation of the filtrate under vacuum affords the compound of formula (XVI) where Z is chloro.

Alternatively, the compound of formula (XII) is reacted as above, substituting an appropriately substituted alkyl or aryl chloroformate, or an appropriately substituted dialkyl or diaryl dicarbonate, for phosgene, giving the compound of formula (XVI) where Z is the correspondingly substituted alkoxy or aryloxy leaving group.

Alternatively, the compound of formula (XII) is reacted as above, substituting N,N'-carbonyldiimidazole for phosgene, giving the compound of formula (XVI) where Z is 1-imidazolyl.

Compounds of formula (Ia) are then prepared by treating the appropriately substituted compound of formula (XVI) with an appropriate amine of formula $HNR^6R^7$, thereby converting the —OC(O)Z group to the corresponding carbamate. To carry out this process, the compound of formula (XVI) is dissolved in an inert solvent as defined above, preferably tetrahydrofuran, and reacted with from about 2–5 molar equivalents, preferably about 2–3 molar equivalents, of the appropriate amine of formula $HNR^6R^7$ in solution in an inert solvent as defined above, preferably tetrahydrofuran. The reaction takes place at a temperature of about 0°–40° C., preferably about 20°–30° C., for about 1–10 hours, preferably about 4–6 hours. When the reaction is substantially complete, the product compound of formula (Ia) is isolated by conventional means such as chromatography.

Alternatively, the reaction is carried out in the presence of from 1–5 molar equivalents, preferably 2 molar equivalents, of a tertiary organic base or an inorganic base, as defined above. The compound of formula (XVI) is then reacted with from 1–4 molar equivalents, preferably about 1.2 molar equivalents, of the appropriate amine of formula $HNR^6R^7$ in an inert organic solvent, as defined above.

Alternatively, as shown in Reaction Sequence IVB, compounds of formula (Ia) are made directly from compounds of formula (XII), by reaction with an appropriately substituted carbamoyl chloride of formula $ClC(O)NR^6R^7$, where $R^6$ and $R^7$ cannot both be hydrogen. To carry out this process, the compound of formula (XII) is dissolved in an inert organic solvent as defined above, preferably tetrahydrofuran, and reacted with from 1–4 molar equivalents, preferably about 1.2 molar equivalents, of the appropriate carbamoyl chloride of formula $ClC(O)NR^6R^7$ in the presence of a tertiary organic base or inorganic base as defined above. The reaction takes place at a temperature of about 0°–40° C., preferably about 20°–30° C., for about 1–10 hours, preferably about 4–6 hours. When the reaction is substantially complete, the product of formula (Ia) is isolated by conventional means such as chromatography.

As shown in Reaction Sequence IVC, compounds of formula (Ia) where $R^6$ is not hydrogen and $R^7$ is hydrogen can be made by reacting a compound of formula (XII) with an appropriately substituted isocyanate of formula $R^6NCO$ where $R^6$ is not hydrogen. To carry out this process, the compound of formula (XII) is dissolved in an inert organic solvent as defined above, preferably tetrahydrofuran, and reacted with from 1–5 molar equivalents, preferably about 1.2 molar equivalents, of an isocyanate of formula $R^6NCO$ in the presence of about 0.2 molar equivalents of 4-dimethylaminopyridine. The reaction takes place at a temperature of about 10°–70° C., preferably about 40°–60° C., for about 4–48 hours, preferably about 20–28 hours. When the reaction is substantially complete, the product of formula (Ia) is isolated by conventional means.

The compounds of formula (Ic) and (Id) where one of X and Y is $R^4$ and the other X or Y is —$C(O)OR^5$ are prepared as shown below in Reaction Sequences VA and VB and the subsequent description. The Reaction Sequences are illustrated by reference to the preparation of the compound of formula (Ic), but are of course equally applicable to the preparation of the compound of formula (Id).

REACTION SEQUENCE VA

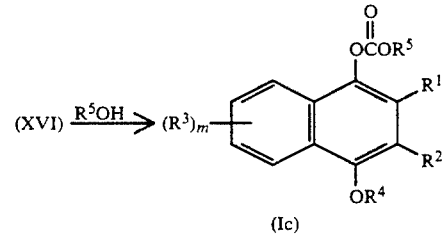

REACTION SEQUENCE VB

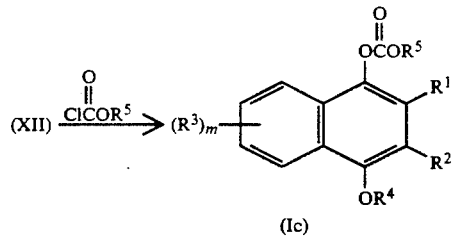

As shown in Reaction Sequence VA, to prepare the compound of formula (Ic), where W is —$OR^5$, the activated carbonyl derivative of formula (XVI), prepared as shown in Reaction Sequence IVA above, is reacted with an alcohol of formula $R^5OH$. To carry out this process, the compound of formula (XVI) is dissolved in an alcohol of formula $R^5OH$ containing from 1–5 molar equivalents, preferably about 2 molar equivalents of a tertiary organic base such as triethylamine or preferably pyridine. The reaction takes place at a temperature of about 0°–40° C., preferably about 20°–30° C., for about 1–10 hours, preferably about 4–6 hours. When the reaction is substantially complete, the product compound of formula (Ic) is isolated by conventional means such as chromatography.

Alternatively, as shown in Reaction Sequence VB, the compound of formula (XII) is reacted as shown above in Reaction Sequence IVA with an appropriate alkyl or aryl chloroformate, or alternatively with an appropriate dialkyl or diaryl dicarbonate, in the presence of a tertiary organic base. For example, the compound of formula (XII) is dissolved in an inert solvent as defined above, preferably tetrahydrofuran, and reacted with a chloroformate and a tertiary organic base, preferably triethylamine. The reaction is conducted at a temperature of about 0°-50° C., preferably about 20°-30° C., for about 4-48 hours, preferably about 16-24 hours, giving the compound of formula (Ic), which is isolated by conventional means such as chromatography.

The compounds of formula (Ib) and (Id) are prepared in the manner shown above for the compounds of formula (Ia) and (Ic), replacing the starting materials of formula (XII) and (XVI) with the compounds of formula (XIII) and (XVII) respectively.

Preparation of Starting Materials

The compounds of formula $HNR^6R^7$ are commercially available from, i.a., Aldrich Chemical Co. Alternatively, they can be prepared by standard methods known to those skilled in the chemical art.

The compounds of formula $ClC(O)NR^6R^7$ are either available commercially from, i.a., Aldrich Chemical Co. or they can be prepared by, for example, reaction of a secondary amine of formula $HNR^6R^7$ with phosgene. Compounds of formula $ClC(O)NR^6R^7$ wherein $R^6$ is hydrogen can be prepared by the reaction of an isocyanate of formula $R^7NCO$ with an excess of dry hydrochloric acid in an inert solvent. These reactions are described in greater detail in *Comprehensive Organic Chemistry*, Vol. 2, by Barton and Ollis, pp. 1088-1090.

Any alkyl or aryl chloroformates that are not commercially available are prepared, for example, by reaction of phosgene with one equivalent of the appropriate alcohol or phenol in the presence of a base. The reactions are described in greater detail in *Comprehensive Organic Chemistry*, by Barton and Ollis, Vol 2, pp 1078-1083 and Vol. 3, pp. 432-4.

The compounds of formula $R^7NCO$ that are not commercially available are prepared by reaction of an appropriately substituted primary amine ($R^7NH_2$) with phosgene. The reaction is discussed in further detail in *Organic Functional Group Preparations*, 2nd Edition, Vol. 1, by Sandler and Karo, pp. 364-365.

In summary, the compounds of the present invention are made by the procedures below:

1. The process for preparing compounds of formula (Ia) and (Ib), wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are either $R^4$ or $-C(O)NR^6R^7$ wherein $R^4$ is lower alkyl of one to six carbon atoms or phenyl-lower-alkyl of one to six carbon atoms, wherein the phenyl ring is optionally substituted by one or two substituents chosen from lower alkyl of one to four carbon atoms, lower alkoxy of one to four carbon atoms and halo; and $R^6$ and $R^7$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

which comprises:

(a) reacting a compound of the formula

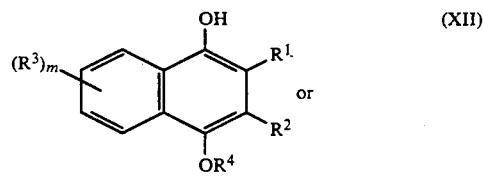

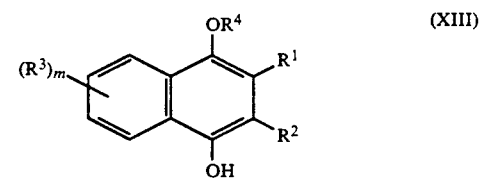

wherein $R^1$, $R^2$, $R^3$, $R^4$ and m are as defined above, with an isocyanate of the formula $R^6NCO$, where $R^6$ is as defined above but is not hydrogen, or (b) reacting a compound of the formula (XII) or (XIII) with a carbamoyl chloride of the formula $ClC(O)NR^6R^7$, where $R^6$ and $R^7$ are as defined above but $R^6$ is not hydrogen.

2. Alternatively, the process for the preparation of the compounds of the formula (Ia) and (Ib), which comprises:

reacting a compound of the formula

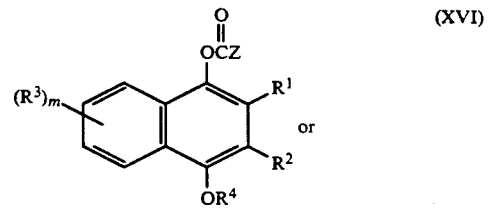

-continued

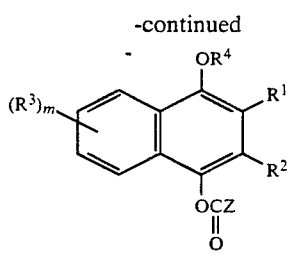
(XVII)

wherein $R^1$, $R^2$, $R^3$, $R^4$ and m are as defined above, and —C(O)Z is an activated carbonyl complex where Z is as defined supra, with an appropriate amine of the formula $HNR^6R^7$, where $R^6$ and $R^7$ are as defined above.

3. The process for the preparation of the compounds of the formulas (Ic) and (Id), where $R^1$, $R^2$, $R^3$, $R^4$ and m are as defined above and X and Y are different and are either $R^4$ or —C(O)OR$^5$, where $R^5$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; which comprises: reacting a compound of the formula

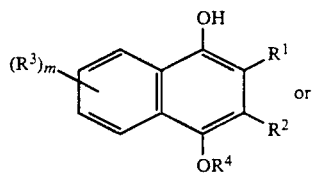
(XII)

or

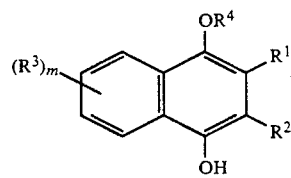
(XIII)

wherein $R^1$, $R^2$, $R^3$, $R^4$ and m are as defined above, with (a) a chloroformate of the formula $ClC(O)OR^5$, where $R^5$ is as defined above, or (b) a dicarbonate of the formula $R^5OC(O)OC(O)OR^5$, where $R^5$ is as defined above.

4. Alternatively, the process for the preparation of the compounds of the formula (Ic) and (Id), which comprises:

reacting a compound of the formula

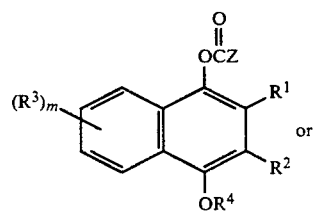
(XVI)

or

-continued

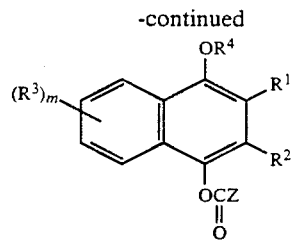
(XVII)

wherein $R^1$, $R^2$, $R^3$, $R^4$ and m are as defined above, and —C(O)Z is an activated carbonyl complex where Z is as defined above, with an appropriate alcohol of the formula $R^5OH$, where $R^5$ is as defined above.

The following specific description is given to enable those skilled in the art to more clearly understand and practice the present invention. It should not be considered as a limitation upon the scope of the invention but merely as illustrative and representative thereof.

PREPARATION 1

A. A solution of 1,4-naphthoquinone (7.91 g), propanoic acid (3.70 g) and silver nitrate (1.53 g) in a mixture of acetonitrile (11.4 mL), sulfolane (34.1 mL) and water (79.5 mL) was heated at 60°–65° C. for 2 hours. A solution of ammonium persulfate (13.7 g) in water (25 mL) was then added dropwise. The mixture was cooled in ice water and extracted with ether. The organic layer was washed with saturated sodium bicarbonate, water and brine, then dried, filtered and evaporated. Chromatography over silica gel afforded 2-ethyl-1,4-naphthoquinone, m.p. 87°–88° C.

B. Similarly, using the above procedure but optionally replacing 1,4-naphthoquinone with an appropriately substituted 1,4-naphthoquinone, or optionally replacing propanoic acid with an appropriate carboxylic acid, the following compounds may be prepared:

2-methyl-1,4-naphthoquinone;
2-n-propyl-1,4-naphthoquinone;
2,6-dimethyl-1,4-naphthoquinone;
2-ethyl-5-methyl-1,4-naphthoquinone;
2-sec-butyl-1,4-naphthoquinone;
2-n-pentyl-1,4-naphthoquinone;
2-ethyl-5-fluoro-1,4-naphthoquinone;
3-ethyl-6-methoxy-1,4-naphthoquinone;
2-methyl-6-benzyloxy-1,4-naphthoquinone;
2-ethyl-6-methoxy-1,4-naphthoquinone;
2-methyl-6-fluoro-1,4-naphthoquinone;
2-isopropyl-1,4-naphthoquinone;
2-n-hexyl-1,4-naphthoquinone;
2-methyl-6-chloro-1,4-naphthoquinone;
2,5-dimethyl-1,4-naphthoquinone;
2-methyl-6-phenyl-1,4-naphthoquinone;
2-methyl-5-methoxy-1,4-naphthoquinone;
2-methyl-5-ethoxy-1,4-naphthoquinone;
2-methyl-6-benzyloxy-1,4-naphthoquinone;
2-ethyl-5-chloro-1,4-naphthoquinone;
2-isopropyl-5-phenyl-1,4-naphthoquinone;
2-n-hexyl-6-methyl-1,4-naphthoquinone;
2-n-propyl-6-chloro-1,4-naphthoquinone;
2-n-propyl-6-fluoro-1,4-naphthoquinone;
2-phenyl-1,4-naphthoquinone;
2,6,7-trimethyl-1,4-naphthoquinone;
2-t-butyl-1,4-naphthoquinone; and
2-n-propyl-6-methyl-1,4-naphthoquinone.

PREPARATION 2

Preparation of compounds of formula (IV)

A. Chlorine was bubbled through a solution of 1,4-naphthoquinone (39.5 g) in glacial acetic acid maintained at 15° C. by cooling. The precipitated intermediate dichloride was isolated by filtration and then suspended in fresh glacial acetic acid (500 mL). Anhydrous sodium acetate (25 g) was added, and the mixture was brought to reflux. Water was then added, and the mixture was allowed to cool, precipitating 2-chloro-1,4-naphthoquinone, collected by filtration and air drying, m.p. 118° C.

B. 2-Chloro-3-methyl-1,4-naphthoquinone was prepared analogously, except that the intermediate dichloride was isolated as an oil after evaporation, aqueous extraction with ether and evaporation. Conversion of this intermediate using sodium acetate in acetic acid gave 2-chloro-3-methyl-1,4-naphthoquinone, m.p. 155°–156° C.

C. Similarly, using the procedure in paragraph A above, but optionally replacing 1,4-naphthoquinone with an appropriately substituted 1,4-naphthoquinone, the following compounds may be prepared:
2-chloro-3,8-dimethyl-1,4-naphthoquinone;
2-chloro-3-methyl-8-methoxy-1,4-naphthoquinone;
2-chloro-3-methyl-7-benzyloxy-1,4-naphthoquinone;
2-chloro-3-ethyl-8-chloro-1,4-naphthoquinone;
2-chloro-3-isopropyl-8-phenyl-1,4-naphthoquinone;
2-chloro-3-n-hexyl-7-methyl-1,4-naphthoquinone;
2-chloro-3-n-propyl-7-chloro-1,4-naphthoquinone;
2-chloro-3-n-propyl-7-fluoro-1,4-naphthoquinone;
2,6-dichloro-1,4-naphthoquinone;
2,5-dichloro-1,4-naphthoquinone;
2-chloro-6-methoxy-1,4-naphthoquinone;
2-chloro-6-ethoxy-1,4-naphthoquinone;
2-chloro-6-methyl-1,4-naphthoquinone;
2-chloro-6-ethyl-1,4-naphthoquinone;
2-chloro-3-ethyl-1,4-naphthoquinone;
2-chloro-3-n-propyl-1,4-naphthoquinone;
2-chloro-3,7-dimethyl-1,4-naphthoquinone;
2-chloro-3-ethyl-8-methyl-1,4-naphthoquinone;
2-chloro-3-phenyl-1,4-naphthoquinone;
2-chloro-3-isopropyl-1,4-naphthoquinone;
2-chloro-3-sec-butyl-1,4-naphthoquinone;
2-chloro-3-n-pentyl-1,4-naphthoquinone;
2-chloro-3-n-hexyl-1,4-naphthoquinone;
2-chloro-3-ethyl-8-fluoro-1,4-naphthoquinone;
2-chloro-3-methyl-7-phenyl-1,4-naphthoquinone;
2-chloro-6-bromo-1,4-naphthoquinone;
2-chloro-6-fluoro-1,4-naphthoquinone;
2-chloro-6-methyl-1,4-naphthoquinone;
2-chloro-6-i-propyl-1,4-naphthoquinone;
2-chloro-6-phenyl-1,4-naphthoquinone;
2-chloro-6-benzyl-1,4-naphthoquinone;
2-chloro-6,7-dimethyl-1,4-naphthoquinone;
2-chloro-5-methoxy-1,4-naphthoquinone;
2-chloro-5-phenyl-1,4-naphthoquinone;
2,7-dichloro-1,4-naphthoquinone;
2-chloro-7-methyl-1,4-naphthoquinone;
2-chloro-3-ethyl-1,4-naphthoquinone;
2-chloro-3-methyl-1,4-naphthoquinone;
2-chloro-3-ethyl-7-methoxy-1,4-naphthoquinone;
2-chloro-3-methyl-6-ethoxy-1,4-naphthoquinone;
2-chloro-3-methyl-7-benzyloxy-1,4-naphthoquinone;
2,6-dichloro-3-methyl-1,4-naphthoquinone;
2-chloro-3,6,7-trimethyl-1,4-naphthoquinone;
2-chloro-3-n-propyl-7-methyl-1,4-naphthoquinone;
2-chloro-3-t-butyl-1,4-naphthoquinone; and
2,6-dichloro-3-n-propyl-1,4-naphthoquinone.

PREPARATION 3

Preparation of compounds of formula (V)

A. A solution of 2-chloro-1,4-naphthoquinone (10.3 g) in tetrahydrofuran (100 mL) was treated with a suspension of sodium methoxide (3.20 g) in tetrahydrofuran (25 mL) at room temperature. After stirring overnight, the mixture was evaporated, and the residue was taken up in ether. The organic layer was washed with brine, dried, filtered and evaporated. Chromatography over silica gel gave 2-methoxy-1,4-naphthoquinone, m.p. 182°–183° C.

B. Similarly, replacing the 2-chloro-1,4-naphthoquinone with other compounds of formula (IV) and following the above procedure, the following compounds were prepared;
2-ethoxy-1,4-naphthoquinone, m.p. 122°–123° C.;
2-methoxy-3-methyl-1,4-naphthoquinone, m.p. 93°–94° C.;
2-n-propoxyl-1,4-naphthoquinone, m.p. 93°–94° C.;
2-isopropoxy-3-methyl-1,4-naphthoquinone, m.p. 114°–115° C.;
2-n-butoxy-1,4-naphthoquinone, m.p. 110°–111° C.;
2-ethoxy-3-methyl-1,4-naphthoquinone, m.p. 67°–68° C.;
2-n-propoxy-3-methyl-1,4-naphthoquinone, oil; and
2-isopropoxy-3-methyl-1,4-naphthoquinone, oil;

C. Similarly, replacing the 2-chloro-1,4-naphthoquinone with other compounds of formula (IV) and following the above procedure, the following compounds are prepared;
2-methoxy-3,8-dimethyl-1,4-naphthoquinone;
2,8-dimethoxy-3-methyl-1,4-naphthoquinone;
2-methoxy-3-methyl-7-benzyloxy-1,4-naphthoquinone;
2-methoxy-3-ethyl-8-chloro-1,4-naphthoquinone;
2-methoxy-3-isopropyl-8-phenyl-1,4-naphthoquinone;
2-methoxy-3-n-hexyl-7-methyl-1,4-naphthoquinone;
2-methoxy-3-n-propyl-7-chloro-1,4-naphthoquinone;
2-methoxy-3-n-propyl-7-fluoro-1,4-naphthoquinone;
2-methoxy-6-chloro-1,4-naphthoquinone;
2-methoxy-5-chloro-1,4-naphthoquinone;
2,6-dimethoxy-1,4-naphthoquinone;
2-methoxy-6-ethoxy-1,4-naphthoquinone;
2-methoxy-6-methyl-1,4-naphthoquinone;
2-methoxy-6-ethyl-1,4-naphthoquinone;
2-methoxy-3-ethyl-1,4-naphthoquinone;
2-methoxy-3-n-propyl-1,4-naphthoquinone;
2-methoxy-3,7-dimethyl-1,4-naphthoquinone;
2-methoxy-3-ethyl-8-methyl-1,4-naphthoquinone;
2-methoxy-3-phenyl-1,4-naphthoquinone;
2-methoxy-3-isopropyl-1,4-naphthoquinone;
2-methoxy-3-sec-butyl-1,4-naphthoquinone;
2-methoxy-3-n-pentyl-1,4-naphthoquinone;
2-methoxy-3-n-hexyl-1,4-naphthoquinone;
2-methoxy-3-ethyl-8-fluoro-1,4-naphthoquinone;
2-methoxy-3-methyl-7-phenyl-1,4-naphthoquinone;
2-methoxy-6-bromo-1,4-naphthoquinone;
2-methoxy-6-fluoro-1,4-naphthoquinone;
2-methoxy-6-methyl-1,4-naphthoquinone;
2-methoxy-6-i-propyl-1,4-naphthoquinone;
2-methoxy-6-phenyl-1,4-naphthoquinone;
2-methoxy-6-benzyl-1,4-naphthoquinone;
2-methoxy-6,7-dimethyl-1,4-naphthoquinone;
2,5-dimethoxy-1,4-naphthoquinone;

2-methoxy-5-phenyl-1,4-naphthoquinone;
2-methoxy-7-chloro-1,4-naphthoquinone;
2-methoxy-7-methyl-1,4-naphthoquinone;
2-methoxy-3-ethyl-1,4-naphthoquinone;
2-methoxy-3-t-butyl-1,4-naphthoquinone;
2,7-dimethoxy-3-ethyl-1,4-naphthoquinone;
2-methoxy-3-methyl-6-ethoxy-1,4-naphthoquinone;
2-methoxy-3-methyl-7-benzyloxy-1,4-naphthoquinone;
2-methoxy-6-chloro-3-methyl-1,4-naphthoquinone;
2-methoxy-3,6,7-trimethyl-1,4-naphthoquinone;
2-methoxy-3-n-propyl-7-methyl-1,4-naphthoquinone;
2-methoxy-6-chloro-3-n-propyl-1,4-naphthoquinone;
2-ethoxy-3-ethyl-1,4-naphthoquinone;
2-ethoxy-3-n-propyl-1,4-naphthoquinone;
2-ethoxy-3-isobutyl-1,4-naphthoquinone;
2-ethoxy-6-bromo-1,4-naphthoquinone;
2-ethoxy-6-fluoro-1,4-naphthoquinone;
2-ethoxy-6-methyl-1,4-naphthoquinone;
2-ethoxy-6-i-propyl-1,4-naphthoquinone;
2-ethoxy-6-phenyl-1,4-naphthoquinone;
2-ethoxy-6-benzyl-1,4-naphthoquinone;
2-ethoxy-6,7-dimethyl-1,4-naphthoquinone;
2-ethoxy-5-methoxy-1,4-naphthoquinone;
2-ethoxy-5-phenyl-1,4-naphthoquinone;
2-ethoxy-6-chloro-1,4-naphthoquinone;
2-ethoxy-7-methyl-1,4-naphthoquinone;
2-ethoxy-3-ethyl-5-fluoro-1,4-naphthoquinone;
2-ethoxy-3-methyl-5-phenyl-1,4-naphthoquinone;
2-n-propoxy-3-ethyl-1,4-naphthoquinone;
2-n-propoxy-3-n-propyl-1,4-naphthoquinone;
2-n-propoxy-3-n-hexyl-1,4-naphthoquinone;
2-isopropoxy-3-ethyl-1,4-naphthoquinone;
2-isopropoxy-3-n-propyl-1,4-naphthoquinone;
2-isopropoxy-3-n-hexyl-1,4-naphthoquinone;
2-n-butoxy-3-methyl-1,4-naphthoquinone;
2-n-butoxy-3-ethyl-1,4-naphthoquinone;
2-s-butoxy-1,4-naphthoquinone;
2-n-pentyloxy-1,4-naphthoquinone;
2-n-pentyloxy-3-methyl-1,4-naphthoquinone;
2-s-pentyloxy-1,4-naphthoquinone;
2-n-hexyloxy-1,4-naphthoquinone;
2-n-hexyloxy-3-methyl-1,4-naphthoquinone;
2(2,2-dimethylpropoxy)-1,4-naphthoquinone;
2-phenoxy-1,4-naphthoquinone;
2-(4-chlorophenoxy)-1,4-naphthoquinone;
2-(4-methoxyphenoxy)-1,4-naphthoquinone;
2-(2,4-dichlorophenoxy)-1,4-naphthoquinone;
2-t-butyloxy-1,4-naphthoquinone; and
2-(3-methylphenoxy)-1,4-naphthoquinone.

Preparation 4

(Preparation of a compound of formula (VII)

A. A solution of 2-methoxy-1,4-naphthoquinone (20.0 g) in tetrahydrofuran (150 mL) was hydrogenated at atmospheric pressure over Pd-C (10%, 0.5 g) until the calculated amount of hydrogen was absorbed, approximately 4 hours. While still under a blanket of hydrogen, a solution of acetic anhydride (20 mL) and pyridine (18 mL) in tetrahydrofuran (50 mL) was added to the mixture. After stirring for 1 hour the catalyst was filtered off and the solvent removed from the filtrate under reduced pressure. The residue was dissolved in ether (100 mL) and was washed with 1M hydrochloric acid (3×50 mL) and with brine (2×50 mL). The organic layer was dried over sodium sulfate, filtered, and evaporated. Recrystallization from ether afforded 2-methoxy-1,4-diacetyloxynaphthalene, m.p. 135°–136° C.

B. Similarly proceeding as above, substituting the appropriate compound of formula (V) for 2-methoxy-1,4-naphthoquinone, where necessary, and the appropriate acid anhydride, where necessary, for acetic anhydride, the following compounds, for example, were prepared:
2-ethoxy-1,4-diacetyloxynaphthalene, m.p. 64° C.;
2-methoxy-3-methyl-1,4-diacetyloxynaphthalene, m.p. 105°–106° C.;
2-methoxy-1,4-dipropionyloxynaphthalene, m.p. 91°–92° C.;
2-methoxy-1,4-di(2,2-dimethylpropionoylyloxy)-naphthalene, m.p. 111°–112° C.;
6- and 7- chloro-2-methoxy-1,4-diacetyloxynaphthalene, m.p. 77°–78° C.;
2-isobutoxy-1,4-diacetyloxynaphthalene;
2-n-butoxy-1,4-diacetyloxynaphthalene;
2-isopropoxy-1,4-diacetyloxynaphthalene, m.p. 69°–70° C.;
2-n-dodecyloxy-1,4-diacetyloxynaphthalene, m.p. 61°–62° C.;
2-phenoxy-1,4-diacetyloxynaphthalene;
2-methoxy-1,4-di(2,2-dimethylpropanoyloxy)naphthalene; m.p. 109°–110° C.;
2-methoxy-1,4-di-i-butanoyloxynaphthalene, m.p. 79°–80° C.;
2-methoxy-1,4-di-n-butanoyloxynaphthalene, m.p. 68° C.;
2-methoxy-1,4-dibenzoyloxynaphthalene;
2-ethoxy-1,4-dipropanoyloxynaphthalene, m.p. 63°–64° C.;
2-ethoxy-1,4-di-i-butanoyloxynaphthalene;
2-ethoxy-1,4-di(2,2-dimethylpropanoyloxy)naphthalene, m.p. 78°–79° C.; and
2-ethoxy-1,4-dibenzoyloxynaphthalene, m.p. 172°–173° C.

Similarly proceeding as above, substituting the appropriate compound of formula (V) for 2-methoxy-1,4-naphthoquinone, where necessary, and the appropriate acid anhydride, where necessary, for acetic anhydride, the following compounds, for example, are prepared:
2-methoxy-3,8-dimethyl-1,4-diacetyloxynaphthalene;
2,8-dimethoxy-3-methyl-1,4-diacetyloxynaphthalene;
2-methoxy-3-methyl-7-benzyloxy-1,4-diacetyloxynaphthalene;
2-methoxy-3-ethyl-8-chloro-1,4-diacetyloxynaphthalene;
2-methoxy-3-isopropyl-8-phenyl-1,4-diacetyloxynaphthalene;
2-methoxy-3-n-hexyl-7-methyl-1,4-diacetyloxynaphthalene;
2-methoxy-3-n-propyl-7-chloro-1,4-diacetyloxynaphthalene;
2-methoxy-3-n-propyl-7-fluoro-1,4-diacetyloxynaphthalene;
2-methoxy-6-chloro-1,4-diacetyloxynaphthalene;
2-methoxy-5-chloro-1,4-diacetyloxynaphthalene;
2,6-dimethoxy-1,4-diacetyloxynaphthalene;
2-methoxy-6-ethoxy-1,4-diacetyloxynaphthalene;
2-methoxy-6-methyl-1,4-diacetyloxynaphthalene;
2-methoxy-6-ethyl-1,4-diacetyloxynaphthalene;
2-methoxy-3-ethyl-1,4-diacetyloxynaphthalene;
2-methoxy-3-n-propyl-1,4-diacetyloxynaphthalene;
2-methoxy-3-t-butyl-1,4-diacetyloxynaphthalene;
2-methoxy-3,7-dimethyl-1,4-diacetyloxynaphthalene;
2-methoxy-3-ethyl-8-methyl-1,4-diacetyloxynaphthalene;
2-methoxy-3-phenyl-1,4-diacetyloxynaphthalene;

2-methoxy-3-isopropyl-1,4-diacetyloxynaphthalene;
2-methoxy-3-sec-butyl-1,4-diacetyloxynaphthalene;
2-methoxy-3-n-pentyl-1,4-diacetyloxynaphthalene;
2-methoxy-3-n-hexyl-1,4-diacetyloxynaphthalene;
2-methoxy-3-ethyl-8-fluoro-1,4-diacetyloxynaphthalene;
2-methoxy-3-methyl-7-phenyl-1,4-diacetyloxynaphthalene;
2-methoxy-6-bromo-1,4-diacetyloxynaphthalene;
2-methoxy-6-fluoro-1,4-diacetyloxynaphthalene;
2-methoxy-6-methyl-1,4-diacetyloxynaphthalene;
2-methoxy-6-i-propyl-1,4-diacetyloxynaphthalene;
2-methoxy-6-phenyl-1,4-diacetyloxynaphthalene;
2-methoxy-6-benzyl-1,4-diacetyloxynaphthalene;
2-methoxy-6,7-dimethyl-1,4-diacetyloxynaphthalene;
2,5-dimethoxy-1,4-diacetyloxynaphthalene;
2-methoxy-5-phenyl-1,4-diacetyloxynaphthalene;
2-methoxy-7-chloro-1,4-diacetyloxynaphthalene;
2-methoxy-7-methyl-1,4-diacetyloxynaphthalene;
2-methoxy-3-ethyl-1,4-diacetyloxynaphthalene;
2-methoxy-5-methyl-1,4-diacetyloxynaphthalene;
2,7-dimethoxy-3-ethyl-1,4-diacetyloxynaphthalene;
2-methoxy-3-methyl-6-ethoxy-1,4-diacetyloxynaphthalene;
2-methoxy-3-methyl-7-benzyloxy-1,4-diacetyloxynaphthalene;
2-methoxy-6-chloro-3-methyl-1,4-diacetyloxynaphthalene;
2-methoxy-3,6,7-trimethyl-1,4-diacetyloxynaphthalene;
2-methoxy-3-n-propyl-7-methyl-1,4-diacetyloxynaphthalene;
2-methoxy-6-chloro-3-n-propyl-1,4-diacetyloxynaphthalene;
2-ethoxy-1,4-diacetyloxynaphthalene;
2-ethoxy-3-methyl-1,4-diacetyloxynaphthalene;
2-ethoxy-3-ethyl-1,4-diacetyloxynaphthalene;
2-ethoxy-3-n-propyl-1,4-diacetyloxynaphthalene;
2-ethoxy-3-isobutyl-1,4-diacetyloxynaphthalene;
2-ethoxy-6-bromo-1,4-diacetyloxynaphthalene;
2-ethoxy-6-fluoro-1,4-diacetyloxynaphthalene;
2-ethoxy-6-methyl-1,4-diacetyloxynaphthalene;
2-ethoxy-6-i-propyl-1,4-diacetyloxynaphthalene;
2-ethoxy-6-phenyl-1,4-diacetyloxynaphthalene;
2-ethoxy-6-benzyl-1,4-diacetyloxynaphthalene;
2-ethoxy-6,7-dimethyl-1,4-diacetyloxynaphthalene;
2-ethoxy-5-methoxy-1,4-diacetyloxynaphthalene;
2-ethoxy-5-phenyl-1,4-diacetyloxynaphthalene;
2-ethoxy-6-chloro-1,4-diacetyloxynaphthalene;
2-ethoxy-7-methyl-1,4-diacetyloxynaphthalene;
2-ethoxy-3-ethyl-5-fluoro-1,4-diacetyloxynaphthalene;
2-ethoxy-3-methyl-5-phenyl-1,4-diacetyloxynaphthalene;
2-n-propoxy-1,4-diacetyloxynaphthalene;
2-n-propoxy-3-methyl-1,4-diacetyloxynaphthalene;
2-n-propoxy-3-ethyl-1,4-diacetyloxynaphthalene;
2-n-propoxy-3-n-propyl-1,4-diacetyloxynaphthalene;
2-n-butoxy-1,4-diacetyloxynaphthalene;
2-n-butoxy-3-methyl-1,4-diacetyloxynaphthalene;
2-n-butoxy-3-ethyl-1,4-diacetyloxynaphthalene;
2-t-butoxy-1,4-diacetyloxynaphthalene;
2-n-pentyloxy-1,4-diacetyloxynaphthalene;
2-n-pentyloxy-3-methyl-1,4-diacetyloxynaphthalene;
2-s-pentyloxy-1,4-diacetyloxynaphthalene;
2-n-hexyloxy-1,4-diacetyloxynaphthalene;
2-n-hexyloxy-3-methyl-1,4-diacetyloxynaphthalene;
2(2,2-dimethylpropoxy)-1,4-diacetyloxynaphthalene;
2-phenoxy-1,4-diacetyloxynaphthalene;
2-(4-chlorophenoxy)-1,4-diacetyloxynaphthalene;
2-(4-methoxyphenoxy)-1,4-diacetyloxynaphthalene;
2-(2,4-dichlorophenoxy)-1,4-diacetyloxynaphthalene;
2-(3-methylphenoxy)-1,4-diacetyloxynaphthalene;
2-methoxy-1,4-dipropanoyloxynaphthalene;
2-methoxy-1,4-dibutanoyloxynaphthalene;
2-methoxy-1,4-dihexanoyloxynaphthalene;
2-methoxy-3-methyl-1,4-dipropanoyloxynaphthalene;
2-ethoxy-1,4-dipropanoyloxynaphthalene;
2-ethoxy-1,4-dibutanoyloxynaphthalene;
2-ethoxy-1,4-dihexanoyloxynaphthalene;
2-ethoxy-3-methyl-1,4-dipropanoyloxynaphthalene; and
2-phenoxy-1,4-dibenzoyloxynaphthalene.

PREPARATION 5

Preparation of compounds of formula (VIII) and (IX)

A. Ten grams of 2-methoxy-1,4-diacetyloxynaphthalene, 150 ml of 0.05M, pH 8, phosphate buffer solution and 150 ml of acetonitrile are heated at 80° C. for 10 days. The reaction is monitored by TLC. Additional disodium hydrogen phosphate is added to maintain the reaction mixture at pH 8. The reaction mixture is cooled and solvent evaporated and the resultant residue is extracted with ethyl acetate (3X), washed with 1M HCl (2X) and brine (2X). The solution is dried over sodium sulfate, filtered and evaporated. The residue is an isomeric mixture from which 1-hydroxy-2-methoxy-4-acetyloxynaphthalene and 1-acetyloxy-2-methoxy-4-hydroxynaphthalene are separated by preparative HPLC on silica gel, eluting with 4% anhydrous methanol in hexane.

B. Similarly, proceeding as in Part A above, substituting the appropriate compound of formula (VII) for 2-methoxy-1,4-diacetyloxynaphthalene the following compounds of formula (VIII) and (IX) are prepared:
1-acetyloxy-2-ethoxy-4-hydroxynaphthalene;
1-hydroxy-2-ethoxy-4-acetyloxynaphthalene;
1-acetyloxy-2-methoxy-3-methyl-4-hydroxynaphthalene;
1-hydroxy-2-methoxy-3-methyl-4-acetyloxynaphthalene;
1-acetyloxy-2-methoxy-3-ethyl-4-hydroxynaphthalene;
1-hydroxy-2-methoxy-3-ethyl-4-acetyloxynaphthalene;
1-acetyloxy-2-methoxy-3-isobutyl-4-hydroxynaphthalene;
1-hydroxy-2-methoxy-3-isobutyl-4-acetyloxynaphthalene;
1-acetyloxy-2-methoxy-3-t-butyl-4-hydroxynaphthalene;
1-hydroxy-2-methoxy-3-t-butyl-4-acetyloxynaphthalene;
1-acetyloxy-2-methoxy-3-n-hexyl-4-hydroxynaphthalene;
1-hydroxy-2-methoxy-3-n-hexyl-4-acetyloxynaphthalene;
1-acetyloxy-2-methoxy-6-bromo-4-hydroxynaphthalene;
1-hydroxy-2-methoxy-6-bromo-4-acetyloxynaphthalene;
1-acetyloxy-2-methoxy-6-fluoro-4-hydroxynaphthalene;
1-hydroxy-2-methoxy-6-fluoro-4-acetyloxynaphthalene;
1-acetyloxy-2-methoxy-6-methyl-4-hydroxynaphthalene;
1-hydroxy-2-methoxy-6-methyl-4-acetyloxynaphthalene;

1-acetyloxy-2-methoxy-6-i-propyl-4-hydroxynaphthalene;
1-hydroxy-2-methoxy-6-i-propyl-4-acetyloxynaphthalene;
1-acetyloxy-2-methoxy-6-phenyl-4-hydroxynaphthalene;
1-hydroxy-2-methoxy-6-phenyl-4-acetyloxynaphthalene;
1-acetyloxy-2-methoxy-6-benzyl-4-hydroxynaphthalene;
1-hydroxy-2-methoxy-6-benzyl-4-acetyloxynaphthalene;
1-acetyloxy-2-methoxy-6,7-dimethyl-4-hydroxynaphthalene;
1-hydroxy-2-methoxy-6,7-dimethyl-4-acetyloxynaphthalene;
1-acetyloxy-2,5-dimethoxy-4-hydroxynaphthalene;
1-hydroxy-2,5-dimethoxy-4-acetyloxynaphthalene;
1-acetyloxy-2-methoxy-5-phenyl-4-hydroxynaphthalene;
1-hydroxy-2-methoxy-5-phenyl-4-acetyloxynaphthalene;
1-acetyloxy-2-methoxy-6-chloro-4-hydroxynaphthalene;
1-hydroxy-2-methoxy-6-chloro-4-acetyloxynaphthalene;
1-acetyloxy-2-methoxy-3-ethyl-5-fluoro-4-hydroxynaphthalene;
1-hydroxy-2-methoxy-3-ethyl-5-fluoro-4-acetyloxynaphthalene;
1-acetyloxy-2-methoxy-3-methyl-5-phenyl-4-hydroxynaphthalene;
1-hydroxy-2-methoxy-3-methyl-5-phenyl-4-acetyloxynaphthalene;
1-acetyloxy-2-methoxy-3-ethyl-6-methoxy-4-hydroxynaphthalene;
1-hydroxy-2-methoxy-3-ethyl-6-methoxy-4-acetyloxynaphthalene;
1-acetyloxy-2-methoxy-3-methyl-6-ethoxy-4-hydroxynaphthalene;
1-hydroxy-2-methoxy-3-methyl-6-ethoxy-4-acetyloxynaphthalene;
1-acetyloxy-2-methoxy-3-methyl-6-benzyloxy-4-hydroxynaphthalene;
1-hydroxy-2-methoxy-3-methyl-6-benzyloxy-4-acetyloxynaphthalene;
1-acetyloxy-2-methoxy-3-methyl-6-chloro-4-hydroxynaphthalene;
1-hydroxy-2-methoxy-3-methyl-6-chloro-4-acetyloxynaphthalene;
1-acetyloxy-2-methoxy-3-ethyl-6-methoxy-4-hydroxynaphthalene;
1-hydroxy-2-methoxy-3-ethyl-6-methoxy-4-acetyloxynaphthalene;
1-acetyloxy-2-methoxy-5-fluoro-3-methyl-4-hydroxynaphthalene;
1-hydroxy-2-methoxy-5-fluoro-3-methyl-4-acetyloxynaphthalene;
1-acetyloxy-2-methoxy-3,6,7-trimethyl-4-hydroxynaphthalene;
1-hydroxy-2-methoxy-3,6,7-trimethyl-4-acetyloxynaphthalene;
1-acetyloxy-2-methoxy-3-n-propyl-6-methyl-4-hydroxynaphthalene;
1-hydroxy-2-methoxy-3-n-propyl-6-methyl-4-acetyloxynaphthalene;
1-acetyloxy-2-methoxy-3-n-propyl-6-chloro-4-hydroxynaphthalene.
1-hydroxy-2-methoxy-3-n-propyl-6-chloro-4-acetyloxynaphthalene.
1-acetyloxy-2-ethoxy-4-hydroxynaphthalene;
1-hydroxy-2-ethoxy-4-acetyloxynaphthalene;
1-acetyloxy-2-ethoxy-3-methyl-4-hydroxynaphthalene;
1-hydroxy-2-ethoxy-3-methyl-4-acetyloxynaphthalene;
1-propionyloxy-2-ethoxy-3-ethyl-4-hydroxynaphthalene;
1-hydroxy-2-ethoxy-3-ethyl-4-propionyloxynaphthalene;
1-propionyloxy-2-ethoxy-3-n-propyl-4-hydroxynaphthalene;
1-hydroxy-2-ethoxy-3-n-propyl-4-propionyloxynaphthalene;
1-propionyloxy-2-ethoxy-3-isobutyl-4-hydroxynaphthalene;
1-hydroxy-2-ethoxy-3-isobutyl-4-propionyloxynaphthalene;
1-propionyloxy-2-ethoxy-6-bromo-4-hydroxynaphthalene;
1-hydroxy-2-ethoxy-6-bromo-4-propionyloxynaphthalene;
1-n-butanoyloxy-2-ethoxy-6-fluoro-4-hydroxynaphthalene;
1-hydroxy-2-ethoxy-6-fluoro-4-n-butanoyloxynaphthalene;
1-n-butanoyloxy-2-ethoxy-6-methyl-4-hydroxynaphthalene;
1-hydroxy-2-ethoxy-6-methyl-4-n-butanoyloxynaphthalene;
1-(2-methylpentanoyl)oxy-2-ethoxy-6-i-propyl-4-hydroxynaphthalene;
1-hydroxy-2-ethoxy-6-i-propyl-4-(2-methylpentanoyl)oxynaphthalene;
1-(2-methylpentanoyl)oxy-2-ethoxy-6-phenyl-4-hydroxynaphthalene;
1-hydroxy-2-ethoxy-6-phenyl-4-(2-methylpentanoyl)oxynaphthalene;
1-n-heptanoyloxy-2-ethoxy-6-benzyl-4-hydroxynaphthalene;
1-hydroxy-2-ethoxy-6-benzyl-4-n-heptanoyloxynaphthalene;
1-hydroxy-2-ethoxy-6,7-dimethyl-4-n-heptanoyloxynaphthalene;
1-(2,2-dimethylpropionyloxy)-2-ethoxy-5-methoxy-4-hydroxynaphthalene;
1-hydroxy-2-ethoxy-5-methoxy-4-(2,2-dimethylpropionyloxy)naphthalene;
1-(2,2-dimethylpropionyloxy)-2-ethoxy-5-phenyl-4-hydroxynaphthalene;
1-hydroxy-2-ethoxy-5-phenyl-4-(2,2-dimethylpropionyloxy)naphthalene;
1-acetyloxy-2-ethoxy-6-chloro-4-hydroxynaphthalene;
1-hydroxy-2-ethoxy-6-chloro-4-acetyloxynaphthalene;
1-acetyloxy-2-ethoxy-7-methyl-4-hydroxynaphthalene;
1-hydroxy-2-ethoxy-7-methyl-4-acetyloxynaphthalene;
1-acetyloxy-2-ethoxy-3-ethyl-5-fluoro-4-hydroxynaphthalene;
1-hydroxy-2-ethoxy-3-ethyl-5-fluoro-4-acetyloxynaphthalene;
1-acetyloxy-2-ethoxy-3-methyl-5-phenyl-4-hydroxynaphthalene;
1-hydroxy-2-ethoxy-3-methyl-5-phenyl-4-acetyloxynaphthalene;
1-acetyloxy-2-n-propoxy-4-hydroxynaphthalene;
1-hydroxy-2-n-propoxy-4-acetyloxynaphthalene;
1-acetyloxy-2-n-propoxy-3-methyl-4-hydroxynaphthalene;

1-hydroxy-2-n-propoxy-3-methyl-4-acetyloxynaphthalene;
1-acetyloxy-2-n-butoxy-4-hydroxynaphthalene;
1-hydroxy-2-n-butoxy-4-acetyloxynaphthalene;
1-acetyloxy-2-t-butoxy-4-hydroxynaphthalene;
1-hydroxy-2-t-butoxy-4-acetyloxynaphthalene;
1-acetyloxy-2-n-hexyloxy-4-hydroxynaphthalene;
1-hydroxy-2-n-hexyloxy-4-acetyloxynaphthalene;
1-acetyloxy-2-phenoxy-4-hydroxynaphthalene;
1-hydroxy-2-phenoxy-4-acetyloxynaphthalene;
1-acetyloxy-2-(4-chlorophenoxy)-4-hydroxynaphthalene;
1-hydroxy-2-(4-chlorophenoxy)-4-hydroxynaphthalene;
1-propionoyloxy-2-methoxy-4-hydroxynaphthalene;
1-hydroxy-2-methoxy-4-propionoyloxynaphthalene;
1-butanoyloxy-2-methoxy-4-hydroxynaphthalene;
1-hydroxy-2-methoxy-4-butanoyloxynaphthalene;
1-hexanoyloxy-2-methoxy-4-hydroxynaphthalene;
1-hydroxy-2-methoxy-4-hexanoyloxynaphthalene;
1-propanoyloxy-2-methoxy-3-methyl-4-hydroxynaphthalene;
1-hydroxy-2-methoxy-3-methyl-4-propanoyloxynaphthalene;
1-propanoyloxy-2-ethoxy-4-hydroxynaphthalene;
1-hydroxy-2-ethoxy-4-propanoyloxynaphthalene;
1-butanoyloxy-2-ethoxy-4-hydroxynaphthalene;
1-hydroxy-2-ethoxy-4-butanoyloxynaphthalene;
1-hexanoyloxy-2-ethoxy-4-hydroxynaphthalene;
1-hydroxy-2-ethoxy-4-hexanoyloxynaphthalene;
1-propanoyloxy-2-propoxy-3-methyl-4-hydroxynaphthalene; and
1-hydroxy-2-propoxy-3-methyl-4-propanoyloxynaphthalene.

PREPARATION 6

(Preparation of compounds of formula (X) and (XI) where one of X and Y is $R^4$ and the other X or Y is —C(O)W).

A. A solution of 1-acetyloxy-2-methoxy-4-hydroxynaphthalene (23.2 g) and methyl iodide (6.4 mL) in tetrahydrofuran (250 mL) was treated dropwise with a solution of DBU (16.5 mL) in tetrahydrofuran (50 mL). The resulting precipitate of DBU.HI was removed by filtration, and the filtrate evaporated. Recrystallization from methanol gave 1-acetyloxy-2,4-dimethoxynaphthalene, m.p. 116°–117° C.

B. Similarly, optionally replacing 1-acetyloxy-2-methoxy-4-hydroxynaphthalene with an appropriate compound of formula (VIII) and optionally replacing methyl iodide with an appropriate alkylating agent, the following compounds of formula (X) were prepared.

1-(2,2-dimethylpropionyloxy)-2,4-dimethoxynaphthalene, m.p. 65°–66° C.;
1-propanoyloxy-2,4-dimethoxynaphthalene, m.p. 83°–84° C.;
1-benzoyloxy-2,4-dimethoxynaphthalene, m.p. 129°–130° C.;
1-propanoyloxy-2,4-diethoxynaphthalene, m.p. 85°–86° C.;
1-acetyloxy-2,4-diethoxynaphthalene, m.p. 114°–115° C.;
1-(2,2-dimethylpropionyloxy)-2,4-diethoxynaphthalene, m.p. 117°–118° C.; and
1-benzoyloxy-2,4-diethoxynaphthalene, m.p. 139°–140° C.

C. Similarly, optionally replacing 1-acetyloxy-2-methoxy-4-hydroxynaphthalene with an appropriate compound of formula (VIII) or (IX) or optionally replacing methyl iodide with an appropriate alkylating agent, the following compounds of formula (X) and (XI) are prepared.

1,2-diethoxy-4-propanoyloxynaphthalene;
1,2-diethoxy-4-acetyloxynaphthalene;
1,2-diethoxy-4-(2,2-dimethylpropionyloxy)naphthalene;
1,2-diethoxy-4-benzoyloxynaphthalene;
1-acetyloxy-2-methoxy-4-ethoxynaphthalene;
1-ethoxy-2-methoxy-4-acetyloxynaphthalene;
1-acetyloxy-2-ethoxy-4-methoxynaphthalene;
1-ethoxy-2-methoxy-4-acetyloxynaphthalene;
1-acetyloxy-2-methoxy-4-propoxynaphthalene;
1-propoxy-2-methoxy-4-acetyloxynaphthalene;
1-acetyloxy-2,4-di-n-butoxynaphthalene;
1,2-di-n-butoxy-4-acetyloxynaphthalene;
1-acetyloxy-2-methoxy-4-n-hexyloxynaphthalene;
1-n-hexyloxy-2-methoxy-4-acetyloxynaphthalene;
1-acetyloxy-2,4-dimethoxy-6-chloronaphthalene;
1,2-dimethoxy-4-acetyloxy-6-chloronaphthalene;
1-n-hexanoyloxy-2,4-dimethoxynaphthalene;
1,2-dimethoxy-4-n-hexanoyloxynaphthalene;
1-phenylacetyloxy-2,4-dimethoxynaphthalene;
1,2-dimethoxy-4-phenylacetyloxynaphthalene;
1-propanoyloxy-2,4-diethoxy-6-chloronaphthalene;
1,2-diethoxy-4-propanoyloxy-6-chloronaphthalene;
1-propanoyloxy-2-ethoxy-4-propoxynaphthalene;
1-propoxy-2-ethoxy-4-propanoyloxynaphthalene;
1-acetyloxy-2,4-dimethoxy-3-methylnaphthalene;
1,2-dimethoxy-3-methyl-4-acetyloxynaphthalene;
1-acetyloxy-2,4-dimethoxy-3-n-butylnaphthalene;
1,2-dimethoxy-3-n-butyl-4-acetyloxynaphthalene;
1-acetyloxy-2,4-dimethoxy-3-methyl-6-chloronaphthalene;
1,2-dimethoxy-3-methyl-4-acetyloxy-6-chloronaphthalene
1-acetyloxy-2,4-dimethoxy-3-n-butyl-5-ethoxynaphthalene
1,2-dimethoxy-3-n-butyl-4-acetyloxy-5-ethoxynaphthalene
1-acetyloxy-2,4-dimethoxy-3-t-butylnaphthalene
1,2-dimethoxy-3-t-butyl-4-acetyloxynaphthalene
1-acetyloxy-2,4-diethoxy-3-methylnaphthalene;
1,2-diethoxy-3-methyl-4-acetyloxynaphthalene;
1-acetyloxy-2,4-diethoxy-3-methyl-6-chloronaphthalene;
1,2-diethoxy-3-methyl-4-acetyloxy-6-chloronaphthalene
1-acetyloxy-2-t-butoxy-4-methoxynaphthalene;
1-methoxy-2-t-butoxy-4-acetyloxynaphthalene
1-acetyloxy-2,4-di-n-hexyloxynaphthalene;
1,2-di-n-hexyloxy-4-acetyloxynaphthalene
1-propanoyloxy-2,4-dimethoxy-3-methyl-6-chloronaphthalene;
1,2-dimethoxy-3-methyl-4-propanoyloxy-6-chloronaphthalene
1-propanoyloxy-2-methoxy-4-propoxynaphthalene; and
1-propoxy-2-methoxy-4-propanoyloxynaphthalene.

PREPARATION 7

(Preparation of compounds of formula (XII) and (XIII))

A. A solution of 1-acetyloxy-2,4-diethoxynaphthalene (2.74 g) in 100 ml of methanol and 10 ml of water was stirred with 2.5 g of potassium carbonate for 6 hours. The solvent was then removed under reduced pressure, and the residue partitioned between ethyl acetate and water. The ethyl acetate layer was dried over anhydrous sodium sulfate and evaporated to a solid, which was recrystallized from ethyl acetate/hexane to give 1-hydroxy-2,4-diethoxynaphthalene, m.p. 83°-84° C.

B. Similarly, replacing 1-acetyloxy-2,4-diethoxynaphthalene with 1-acetyloxy-2,4-dimethoxynaphthalene, the following compound of formula (XII) was prepared:
1-hydroxy-2,4-dimethoxynaphthalene, m.p. 87°-88° C.;

C. Similarly, replacing 1-acetyloxy-2,4-diethoxynaphthalene with other compounds of formula (X) or (XI), the following compounds of formula (XII) and (XIII) are prepared:
1,2-diethoxy-4-hydroxynaphthalene;
1,2-dimethoxy-4-hydroxynaphthalene;
1-hydroxy-2,4-di-n-propoxynaphthalene;
1,2-di-n-propoxy-4-hydroxynaphthalene;
1-hydroxy-2-t-butoxy-4-methoxynaphthalene;
1-methoxy-2-t-butoxy-4-hydroxynaphthalene;
1-hydroxy-2,4-di-n-hexyloxynaphthalene;
1,2-di-n-hexyloxy-4-hydroxynaphthalene;
1-hydroxy-2,4-dimethoxy-3-methylnaphthalene;
1,2-dimethoxy-4-hydroxy-3-methylnaphthalene;
1-hydroxy-2,4-dimethoxy-3-n-butylnaphthalene;
1,2-dimethoxy-4-hydroxy-3-n-butylnaphthalene;
1-hydroxy-2,4-dimethoxy-6-chloronaphthalene;
1,2-dimethoxy-4-hydroxy-6-chloronaphthalene;
1-hydroxy-2,4-diethoxy-6-ethylnaphthalene;
1,2-diethoxy-4-hydroxy-6-ethylnaphthalene;
1-hydroxy-2,4-diethoxy-6-phenylnaphthalene;
1,2-diethoxy-4-hydroxy-6-phenylnaphthalene;
1-hydroxy-2,4-di-n-propoxy-5-methoxynaphthalene;
1,2-di-n-propoxy-4-hydroxy-5-methoxynaphthalene;
1-hydroxy-2-methoxy-4-ethoxynaphthalene;
1-ethoxy-2-methoxy-4-hydroxynaphthalene;
1-hydroxy-2-ethoxy-4-methoxynaphthalene;
1-methoxy-2-ethoxy-4-hydroxynaphthalene;
1-hydroxy-2-methoxy-4-n-propoxynaphthalene;
1-n-propoxy-2-methoxy-4-hydroxynaphthalene;
1-hydroxy-2-ethoxy-4-n-hexyloxynaphthalene;
1-n-hexyloxy-2-ethoxy-4-hydroxynaphthalene;
1-hydroxy-2-n-pentyloxy-4-n-hexyloxynaphthalene;
1-n-hexyloxy-2-n-pentyloxy-4-hydroxynaphthalene;
1-hydroxy-2-phenoxy-4-methoxynaphthalene;
1-methoxy-2-phenoxy-4-hydroxynaphthalene;
1-hydroxy-2-methoxy-3-methyl-4-ethoxynaphthalene;
1-ethoxy-2-methoxy-3-methyl-4-hydroxynaphthalene;
1-hydroxy-2-ethoxy-4-methoxy-6-chloronaphthalene;
1-methoxy-2-ethoxy-4-hydroxy-6-chloronaphthalene;
1-hydroxy-2,6-dimethoxy-4-n-propoxynaphthalene;
1-n-propoxy-2,6-dimethoxy-4-hydroxynaphthalene;

PREPARATION 8

(Alternative preparation of compounds of formula (XII))

A. A solution of 18.9 g of 2-methoxynaphthoquinone in methanol was added slowly to a solution of 34.8 g of sodium hydrosulfite in methanol and the mixture stirred for 1 hour. The solvent was removed under reduced pressure and the residue partitioned between ethyl acetate and water. The organic layer was dried over anhydrous sodium sulfate and evaporated to a purple solid. The solid was dissolved in 200 ml of methanol previously saturated with anhydrous hydrochloric acid and stirred for 3 minutes at 60° C. The mixture was then diluted with 200 ml of ice water and the precipitate filtered off, dried under vacuum and recrystallized from ether/pentane to give 13.25 g of 1-hydroxy-2,4-dimethoxynaphthalene, m.p. 87°-88° C.

B. Similarly 1-hydroxy-2,4-diethoxynaphthalene, m.p. 83°-84° C. is prepared.

C. Similarly, replacing 2-methoxynaphthoquinone with other compounds of formula (V), the following compounds of formula (XII) are prepared:
1-hydroxy-2,4-dimethoxynaphthalene;
1-hydroxy-2,4-di-n-propoxynaphthalene;
1-hydroxy-2,4-di-(2,2-dimethylpropionyloxy)-naphthalene;
1-hydroxy-2,4-di-n-hexyloxynaphthalene;
1-hydroxy-2,4-dimethoxy-3-methylnaphthalene;
1-hydroxy-2,4-dimethoxy-3-n-butylnaphthalene;
1-hydroxy-2,4-dimethoxy-6-chloronaphthalene;
1-hydroxy-2,4-dimethoxy-6-phenylnaphthalene;
1-hydroxy-2,4-diethoxy-6-ethylnaphthalene;
1-hydroxy-2,4-diethoxy-6-phenylnaphthalene; and
1-hydroxy-2,4-di-n-propoxy-5-methoxynaphthalene;

EXAMPLE 1

Preparation of Compounds of Formula (Ia) and (Ib) where $R^7$ is hydrogen

A. To a solution of 1.00 g of 1-hydroxy-2,4-dimethoxynaphthalene, prepared as shown in Preparations 7 and 8, in 50 ml of tetrahydrofuran was added 0.335 g of methyl isocyanate followed by 0.12 g of 4-dimethylaminopyridine. The solution was stirred at room temperature overnight. The solvent was removed under reduced pressure and the residue dissolved in ethyl acetate, washed with dilute hydrochloric acid and dried over anhydrous sodium sulfate. The solvent was removed under reduced pressure and the residue chromatographed on silica gel, eluting with methylene chloride, giving 1-methylcarbamoyloxy-2,4-dimethoxynaphthalene, m.p. 131°-133° C.

B. Similarly, starting with the appropriate compound of formula (XII) and the appropriate isocyanate, the following compounds of formula (Ia) were prepared:
1-ethylcarbamoyloxy-2,4-dimethoxynaphthalene, m.p. 141°-142° C.
1-methylcarbamoyloxy-2,4-diethoxynaphthalene, m.p. 142°-143° C.
1-ethylcarbamoyloxy-2,4-diethoxynaphthalene, m.p. 136°-137° C.

C. Similarly, optionally replacing 1-hydroxy-2,4-methoxynaphthalene with other compounds of formula (XII) or (XIII), and optionally replacing methyl isocyanate with an appropriately substituted isocyanate, the following compounds of formula (Ia) and (Ib) are prepared:
1,2-diethoxy-4-methylcarbamoyloxynaphthalene;
1,2-dimethoxy-4-methylcarbamoyloxynaphthalene;
1,2-diethoxy-4-ethylcarbamoyloxynaphthalene;
1,2-dimethoxy-4-ethylcarbamoyloxynaphthalene;
1-n-propylcarbamoyloxy-2,4-dimethoxynaphthalene
1,2-dimethoxy-4-n-propylcarbamoyloxynaphthalene;
1-n-butylcarbamoyloxy-2,4-dimethoxynaphthalene;
1,2-dimethoxy-4-n-butylcarbamoyloxynaphthalene;
1-t-butylcarbamoyloxy-2,4-dimethoxynaphthalene;
1,2-dimethoxy-4-t-butylcarbamoyloxynaphthalene;
1-n-hexylcarbamoyloxy-2,4-dimethoxynaphthalene;
1,2-dimethoxy-4-n-hexylcarbamoyloxynaphthalene;
1-(2-methylhexyl)carbamoyloxy-2,4-dimethoxynaphthalene;
1,2-dimethoxy-4-(2-methylhexyl)carbamoyloxynaphthalene;

1-phenylcarbamoyloxy-2,4-dimethoxynaphthalene;
1,2-dimethoxy-4-phenylcarbamoyloxynaphthalene;
1-benzylcarbamoyloxy-2,4-dimethoxynaphthalene;
1,2-dimethoxy-4-benzylcarbamoyloxynaphthalene;
1-n-propylcarbamoyloxy-2,4-diethoxynaphthalene
1,2-diethoxy-4-n-propylcarbamoyloxynaphthalene;
1-n-butylcarbamoyloxy-2,4-diethoxynaphthalene;
1,2-diethoxy-4-n-butylcarbamoyloxynaphthalene;
1-t-butylcarbamoyloxy-2,4-diethoxynaphthalene;
1,2-diethoxy-4-t-butylcarbamoyloxynaphthalene;
1-n-hexylcarbamoyloxy-2,4-diethoxynaphthalene;
1,2-diethoxy-4-n-hexylcarbamoyloxynaphthalene;
1-(2-methylhexyl)carbamoyloxy-2,4-diethoxynaphthalene;
1,2-diethoxy-4-(2-methylhexyl)carbamoyloxynaphthalene;
1-phenylcarbamoyloxy-2,4-diethoxynaphthalene;
1,2-diethoxy-4-phenylcarbamoyloxynaphthalene;
1-benzylcarbamoyloxy-2,4-diethoxynaphthalene;
1,2-diethoxy-4-benzylcarbamoyloxynaphthalene;
1-methylcarbamoyloxy-2,4-di-n-propoxynaphthalene;
1,2-di-n-propoxy-4-methylcarbamoyloxynaphthalene;
1-n-propylcarbamoyloxy-2,4-di-n-propoxynaphthalene
1,2-n-propoxy-4-di-n-propylcarbamoyloxynaphthalene;
1-n-butylcarbamoyloxy-2,4-di-n-propoxynaphthalene;
1,2-di-n-propoxy-4-n-butylcarbamoyloxynaphthalene;
1-phenylcarbamoyloxy-2,4-di-n-propoxynaphthalene;
1,2-di-n-propoxy-4-phenylcarbamoyloxynaphthalene;
1-benzylcarbamoyloxy-2,4-di-n-propoxynaphthalene;
1,2-di-n-propoxy-4-benzylcarbamoyloxynaphthalene;
1-methylcarbamoyloxy-2-t-butoxy-4-methoxynaphthalene;
1-methoxy-2-t-butoxy-4-methylcarbamoyloxynaphthalene;
1-ethylcarbamoyloxy-2-t-butoxy-4-methoxynaphthalene;
1-methoxy-2-t-butoxy-4-ethylcarbamoyloxynaphthalene;
1-methylcarbamoyloxy-2,4-di-n-hexyloxynaphthalene;
1,2-di-n-hexyloxy-4-methylcarbamoyloxynaphthalene;
1-methylcarbamoyloxy-2,4-dimethoxy-3-methylnaphthalene;
1,2-dimethoxy-4-methylcarbamoyloxy-3-methylnaphthalene;
1-methylcarbamoyloxy-2,4-dimethoxy-3-n-butylnaphthalene;
1,2-dimethoxy-4-methylcarbamoyloxy-3-n-butylnaphthalene;
1-methylcarbamoyloxy-2,4-dimethoxy-6-chloronaphthalene;
1,2-dimethoxy-4-methylcarbamoyloxy-6-chloronaphthalene;
1-methylcarbamoyloxy-2,4-diethoxy-6-ethylnaphthalene;
1,2-diethoxy-4-methylcarbamoyloxy-6-ethylnaphthalene;
1-methylcarbamoyloxy-2,4-diethoxy-6-phenylnaphthalene;
1,2-diethoxy-4-methylcarbamoyloxy-6-phenylnaphthalene;
1-methylcarbamoyloxy-2,4-di-n-propoxy-5-methoxynaphthalene;
1,2-di-n-propoxy-4-methylcarbamoyloxy-5-methoxynaphthalene;
1-methylcarbamoyloxy-2-methoxy-4-ethoxynaphthalene;
1-ethoxy-2-methoxy-4-methylcarbamoyloxynaphthalene;
1-methylcarbamoyloxy-2-ethoxy-4-methoxynaphthalene;
1-methoxy-2-ethoxy-4-methylcarbamoyloxynaphthalene;
1-methylcarbamoyloxy-2-methoxy-4-n-propoxynaphthalene;
1-n-propoxy-2-methoxy-4-methylcarbamoyloxynaphthalene;
1-methylcarbamoyloxy-2-ethoxy-4-n-hexyloxynaphthalene;
1-n-hexyloxy-2-ethoxy-4-methylcarbamoyloxynaphthalene;
1-methylcarbamoyloxy-2-n-pentyloxy-4-n-hexyloxynaphthalene;
1-n-hexyloxy-2-n-pentyloxy-4-methylcarbamoyloxynaphthalene;
1-methylcarbamoyloxy-2-phenoxy-4-methoxynaphthalene;
1-methoxy-2-phenoxy-4-methylcarbamoyloxynaphthalene;
1-methylcarbamoyloxy-2-methoxy-3-methyl-4-ethoxynaphthalene;
1-ethoxy-2-methoxy-3-methyl-4-methylcarbamoyloxynaphthalene;
1-methylcarbamoyloxy-2-ethoxy-4-methoxy-6-chloronaphthalene;
1-methoxy-2-ethoxy-4-methylcarbamoyloxy-6-chloronaphthalene; and
1-methylcarbamoyloxy-2,6-dimethoxy-4-n-propoxynaphthalene.

EXAMPLE 2

Alternative preparation of compounds of Formula (Ia) and (Ib)

To a solution of 1.27 g of 1-hydroxy-2,4-dimethoxynaphthalene, prepared as shown in Preparations 7 and 8, in 50 ml of tetrahydrofuran and 1 ml of pyridine is added 10 ml of a solution of 12.5% phosgene in benzene. The mixture is stirred overnight at 25° C., filtered and the filtrate evaporated under vacuum to afford crude 1-chlorocarbonyloxy-2,4-dimethoxynaphthalene. This chloroformate is dissolved in 50 ml of dry tetrahydrofuran and a solution of 1.14 g of diethylamine in 10 ml of tetrahydrofuran added. After 4 hours at room temperature the reaction mixture is diluted with ethyl acetate and washed with dilute hydrochloric acid. The organic phase is dried over sodium sulfate and solvent removed under reduced pressure to yield 1-diethylcarbamoyloxy-2,4-dimethoxynaphthalene.

B. Similarly, optionally replacing 1-hydroxy-2,4-dimethoxynaphthalene with other compounds of formula (XII) or (XIII), and optionally replacing diethylamine with an appropriately substituted amine, the following compounds of formula (Ia) and (Ib) are prepared:
1-methylcarbamoyloxy-2,4-dimethoxynaphthalene;
1,2-dimethoxy-4-methylcarbamoyloxynaphthalene;
1-methylcarbamoyloxy-3-methyl-2,4-dimethoxynaphthalene;
1,2-dimethoxy-3-methyl-4-methylcarbamoyloxynaphthalene;
1-dimethylcarbamoyloxy-3-n-hexyl-2,4-dimethoxynaphthalene;
1,2-dimethoxy-3-n-hexyl-4-dimethylcarbamoyloxynaphthalene;
1-dimethylcarbamoyloxy-2,4-dimethoxynaphthalene;
1,2-dimethoxy-4-dimethylcarbamoyloxynaphthalene;

1-n-hexylcarbamoyloxy-2,4-dimethoxynaphthalene;
1,2-dimethoxy-4-n-hexylcarbamoyloxynaphthalene;
1-methylcarbamoyloxy-2,4-dimethoxy-6-chloronaphthalene;
1,2-dimethoxy-4-methylcarbamoyloxy-6-chloronaphthalene;
1-dimethylcarbamoyloxy-2,4-dimethoxy-6-fluoronaphthalene;
1,2-dimethoxy-4-dimethylcarbamoyloxy-6-fluoronaphthalene;
1-(N-methyl-N-hexyl)carbamoyloxy-2,4-dimethoxynaphthalene;
1,2-dimethoxy-4-(N-methyl-N-hexylcarbamoyloxynaphthalene;
1-methylcarbamoyloxy-2,4-diethoxynaphthalene;
1,2-diethoxy-4-methylcarbamoyloxynaphthalene;
1-diethylcarbamoyloxy-3-ethyl-2,4-diethoxynaphthalene;
1,2-diethoxy-3-ethyl-4-diethylcarbamoyloxynaphthalene;
1-dihexylcarbamoyloxy-2,4-diethoxy-6-chloronaphthalene;
1,2-diethoxy-4-dihexylcarbamoyloxy-6-chloronaphthalene;
1-methylcarbamoyloxy-2,4-diethoxy-6,7-dimethylnaphthalene;
1,2-diethoxy-4-methylcarbamoyloxy-6,7-dimethylnaphthalene;
1-methylcarbamoyloxy-2,4-di-n-hexyloxynaphthalene;
1,2-di-n-hexyloxy-4-methylcarbamoyloxynaphthalene;
1-dimethylcarbamoyloxy-2-phenoxy-4-methoxynaphthalene; and
1-methoxy-2-phenoxy-4-dimethylcarbamoyloxynaphthalene.

EXAMPLE 3

Preparation of Compounds of Formula (Ic) and (Id)

To a solution of 1.27 g of 1-hydroxy-2,4-dimethoxynaphthalene, prepared as shown in Preparations 7 and 8, in 50 ml of tetrahydrofuran was added 0.694 g of methyl chloroformate followed by 0.743 g of triethylamine. The mixture was stirred at room temperature for 16 hours, filtered, then the solvent removed under reduced pressure. The residue was dissolved in diethyl ether, washed with dilute hydrochloric acid and dried over anhydrous sodium sulfate. The ether was removed under reduced pressure and the residue chromatographed on silica gel, eluting with a 1:1 mixture of methylene chloride and hexane, to give 1-methoxycarbonyloxy-2,4-dimethoxynaphthalene, m.p. 128°–129° C.

B. Similarly, starting with the appropriate compound of formula (XII) and the appropriate chloroformate of formula ClC(O)OR$^5$, the following compounds of formula (Ic) were prepared:
1-ethoxycarbonyloxy-2,4-dimethoxynaphthalene, m.p. 118°–119° C.
1-benzyloxycarbonyloxy-2,4-dimethoxynaphthalene, m.p. 105°–106° C.
1-methoxycarbonyloxy-2,4-diethoxynaphthalene, m.p. 64°–65° C.
1-ethoxycarbonyloxy-2,4-diethoxynaphthalene, m.p. 86°–87° C.

C. Similarly, optionally replacing 1-hydroxy-2,4-dimethoxynaphthalene with other compounds of formula (XII) or (XIII), and optionally replacing methyl chloroformate with an appropriately substituted chloroformate of formula ClC(O)OR$^5$ or an appropriately substituted dicarbonate of formula R$^5$OC(O)OC(O)OR$^5$, the following compounds of formula (Ic) and (Id) are prepared:
1,2-diethoxy-4-methoxycarbonyloxynaphthalene;
1,2-dimethoxy-4-methoxycarbonyloxynaphthalene;
1,2-diethoxy-4-ethoxycarbonyloxynaphthalene;
1,2-dimethoxy-4-ethoxycarbonyloxynaphthalene;
1-n-propoxycarbonyloxy-2,4-dimethoxynaphthalene
1,2-dimethoxy-4-n-propoxycarbonyloxynaphthalene;
1-n-butoxycarbonyloxy-2,4-dimethoxynaphthalene;
1,2-dimethoxy-4-n-butoxycarbonyloxynaphthalene;
1-t-butoxycarbonyloxy-2,4-dimethoxynaphthalene;
1,2-dimethoxy-4-t-butoxycarbonyloxynaphthalene;
1-n-hexyloxycarbonyloxy-2,4-dimethoxynaphthalene;
1,2-dimethoxy-4-n-hexyloxycarbonyloxynaphthalene;
1-(2-methylhexyloxy)carbonyloxy-2,4-dimethoxynaphthalene;
1,2-dimethoxy-4-(2-methylhexyloxy)carbonyloxynaphthalene;
1-phenoxycarbonyloxy-2,4-dimethoxynaphthalene;
1,2-dimethoxy-4-phenoxycarbonyloxynaphthalene;
1-benzyloxycarbonyloxy-2,4-dimethoxynaphthalene;
1,2-dimethoxy-4-benzyloxycarbonyloxynaphthalene;
1-n-propoxycarbonyloxy-2,4-diethoxynaphthalene;
1,2-diethoxy-4-n-propoxycarbonyloxynaphthalene;
1-n-butoxycarbonyloxy-2,4-diethoxynaphthalene;
1,2-diethoxy-4-n-butoxycarbonyloxynaphthalene;
1-t-butoxycarbonyloxy-2,4-diethoxynaphthalene;
1,2-diethoxy-4-t-butoxycarbonyloxynaphthalene;
1-n-hexyloxycarbonyloxy-2,4-diethoxynaphthalene
1,2-diethoxy-4-n-hexyloxycarbonyloxynaphthalene;
1-(2-methylhexyloxy)carbonyloxy-2,4-diethoxynaphthalene;
1,2-diethoxy-4-(2-methylhexyloxy)carbonyloxynaphthalene;
1-phenoxycarbonyloxy-2,4-diethoxynaphthalene;
1,2-diethoxy-4-phenoxycarbonyloxynaphthalene;
1-benzyloxycarbonyloxy-2,4-diethoxynaphthalene;
1,2-diethoxy-4-benzyloxycarbonyloxynaphthalene;
1-methoxycarbonyloxy-2,4-di-n-propoxynaphthalene;
1,2-di-n-propoxy-4-methoxycarbonyloxynaphthalene;
1-n-propoxycarbonyloxy-2,4-di-n-propoxynaphthalene
1,2-n-propoxy-4-di-n-propoxycarbonyloxynaphthalene;
1-n-butoxycarbonyloxy-2,4-di-n-propoxynaphthalene;
1,2-di-n-propoxy-4-n-butoxycarbonyloxynaphthalene;
1-phenoxycarbonyloxy-2,4-di-n-propoxynaphthalene;
1,2-di-n-propoxy-4-phenoxycarbonyloxynaphthalene;
1-benzoxycarbonyloxy-2,4-di-n-propoxynaphthalene;
1,2-di-n-propoxy-4-benzoxycarbonyloxynaphthalene;
1-methoxycarbonyloxy-2-t-butoxy-4-methoxynaphthalene;
1-methoxy-4-t-butoxy-4-methoxycarbonyloxynaphthalene;
1-ethoxycarbonyloxy-2-t-butoxy-4-methoxynaphthalene;
1-methoxy-4-t-butoxy-4-ethoxycarbonyloxynaphthalene;
1-methoxycarbonyloxy-2,4-di-n-hexyloxynaphthalene;
1,2-di-n-hexyloxy-4-methoxycarbonyloxynaphthalene;
1-methoxycarbonyloxy-2,4-dimethoxy-3-methylnaphthalene;
1,2-dimethoxy-4-methoxycarbonyloxy-3-methylnaphthalene;
1-methoxycarbonyloxy-2,4-dimethoxy-3-n-butylnaphthalene;
1,2-dimethoxy-4-methoxycarbonyloxy-3-n-butylnaphthalene;

1-methoxycarbonyloxy-2,4-dimethoxy-6-chloronaphthalene;

1,2-dimethoxy-4-methoxycarbonyloxy-6-chloronaphthalene;

1-methoxycarbonyloxy-2,4-diethoxy-6-ethylnaphthalene;

1,2-diethoxy-4-methoxycarbonyloxy-6-ethylnaphthalene;

1-methoxycarbonyloxy-2,4-diethoxy-6-phenylnaphthalene;

1,2-diethoxy-4-methoxycarbonyloxy-6-phenylnaphthalene;

1-methoxycarbonyloxy-2,4-d-n-propoxy-5-methoxynaphthalene;

1,2-di-n-propoxy-4-methoxycarbonyloxy-5-methoxynaphthalene;

1-methoxycarbonyloxy-2-methoxy-4-ethoxynaphthalene;

1-ethoxy-2-methoxy-4-methoxycarbonyloxynaphthalene;

1-methoxycarbonyloxy-2-ethoxy-4-methoxynaphthalene;

1-methoxy-2-ethoxy-4-methoxycarbonyloxynaphthalene;

1-methoxycarbonyloxy-2-methoxy-4-n-propoxynaphthalene;

1-n-propoxy-2-methoxy-4-methoxycarbonyloxynaphthalene;

1-methoxycarbonyloxy-2-ethoxy-4-n-hexyloxynaphthalene;

1-n-hexyloxy-2-ethoxy-4-methoxycarbonyloxynaphthalene;

1-methoxycarbonyloxy-2-n-pentyloxy-4-n-hexyloxynaphthalene;

1-n-hexyloxy-2-n-pentyloxy-4-methoxycarbonyloxynaphthalene;

1-methoxycarbonyloxy-2-phenoxy-4-methoxynaphthalene;

1-methoxy-2-phenoxy-4-methoxycarbonyloxynaphthalene;

1-methoxycarbonyloxy-2-methoxy-3-methyl-4-ethoxynaphthalene;

1-ethoxy-2-methoxy-3-methyl-4-methoxycarbonyloxynaphthalene;

1-methoxycarbonyloxy-2-ethoxy-4-methoxy-6-chloronaphthalene;

1-methoxy-2-ethoxy-4-methoxycarbonyloxy-6-chloronaphthalene;

1-methoxycarbonyloxy-2,6-dimethoxy-4-n-propoxynaphthalene;

EXAMPLE 4

Biological Data

1. Test for Topical Anti-Inflammatory Activity by Inhibition of Arachidonic Acid Induced Mouse Ear Edema Materials and Methods Male or female Swiss Webster mice weighing 18-27 g were randomly assigned to treatment groups of 8 or 10 animals, caged together, and given food and water ad libitum.

The test materials were prepared as solutions or suspensions in reagent grade acetone at a dose level of 100 mg/ml and arachidonic acid was prepared as a solution in acetone also at 100 mg/ml. The test materials were applied to the right ears of mice by means of an automatic microliter pipet so that 10 μl of solution was applied to each of the inner and outer surfaces. Each ear therefore received a total of 20 μl of solution containing 2 mg of test material. One hour after application of the test material, the arachidonic acid solution was applied in the same manner. One hour after the arachidonic acid application the animals were sacrificed by cervical dislocation and the right ears were removed. An 8 mm disc was punched from each ear with a biopsy punch, and the discs were weighed to the nearest 0.1 mg. For the purpose of determining the anti-inflammatory effect of test materials a negative control group receiving two applications of acetone only, and a positive control group receiving acetone alone followed by arachidonic acid were run in each experiment. The percent inhibition resulting from treatment with the test material was calculated as follows:

$$\% \text{ Inhib.} = \frac{\text{Plug wt. (Pos. Control)} - \text{Plug wt. (Treated)}}{\text{Plug wt. (Pos. Control)} - \text{Plug wt. (Neg. control)}} \times 100$$

2. Test for Oral Anti-Inflammatory Activity by Oxazolone-Induced Delayed Hypersensitivity Mouse Ear Edema Materials and Methods Female Sim:(SW)fBR mice weighing 23-27 g were used in groups of 10. On days 1 and 2 mice received 50 ul of a 2% solution of oxazolone in acetone applied to the unshaved abdomen (sensitization). On day 6 25 ul of a 1.5% solution of oxazolone in acetone was applied to each side of the right ear (challenge). Test materials were administered orally in aqueous vehicle 1 hr before challenge and again 6 hr after challenge. On day 7, 24 hr after challenge, the mice were euthanized and 8 mm diameter plugs obtained from the ears were weighed.

What is claimed is:

1. A method for treating a mammal having a disease-state which is alleviated by treatment with a lipoxygenase inhibitor, which comprises systemically administering a therapeutically effective amount of a compound of the formula

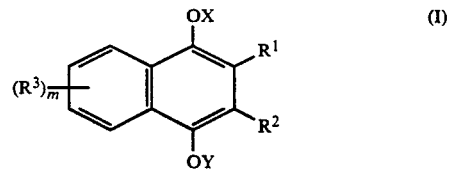

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X and Y are different and are either $R^4$ or —C(O)W wherein $R^4$ is lower alkyl of one to six carbon atoms or phenyl-lower-alkyl of one to six carbon atoms, wherein the phenyl ring is optionally substituted by one or two substituents chosen from lower alkyl of one to four carbon atoms, lower alkoxy of one to four carbon atoms and halo; and W is —$OR^5$ or —$NR^6R^7$, wherein $R^5$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^6$ and $R^7$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

2. The method of claim 1, wherein said disease-state is inflammation.

* * * * *